US009918986B2

(12) United States Patent
Mason et al.

(10) Patent No.: US 9,918,986 B2
(45) Date of Patent: Mar. 20, 2018

(54) METHODS AND COMPOUNDS FOR PREVENTING OSTEOARTHRITIS

(71) Applicants: UNIVERSITY COLLEGE CARDIFF CONSULTANTS LIMITED, South Glamorgan (GB); Deborah Mason, Hereford and Worcester (GB); Cleo Bonnet, Cardiff (GB)

(72) Inventors: Deborah Mason, Hereford and Worcester (GB); Cleo Bonnet, Cardiff (GB)

(73) Assignee: UNIVERSITY COLLEGE CARDIFF CONSULTANTS LIMITED, Cardiff, Wales (GB)

( * ) Notice: Subject to any disclaimer, the term of this patent is extended or adjusted under 35 U.S.C. 154(b) by 0 days.

(21) Appl. No.: 14/902,050

(22) PCT Filed: Jul. 3, 2014

(86) PCT No.: PCT/GB2014/052030
§ 371 (c)(1),
(2) Date: Dec. 30, 2015

(87) PCT Pub. No.: WO2015/001349
PCT Pub. Date: Jan. 8, 2015

(65) Prior Publication Data
US 2017/0035754 A1 Feb. 9, 2017

(30) Foreign Application Priority Data

Jul. 4, 2013 (GB) .................................. 1311984.7

(51) Int. Cl.
*A61K 31/44* (2006.01)
*A61K 31/498* (2006.01)
(Continued)

(52) U.S. Cl.
CPC .......... *A61K 31/498* (2013.01); *A61K 9/0019* (2013.01); *A61K 45/06* (2013.01); *A61K 9/0014* (2013.01)

(58) Field of Classification Search
CPC .. A61K 31/498; A61K 9/0014; A61K 9/0019; A61K 45/06
(Continued)

(56) References Cited

U.S. PATENT DOCUMENTS

| 6,559,293 B1 | 5/2003 | Almarsson et al. |
| 2005/0014847 A1 | 1/2005 | Gaida et al. |
| 2013/0165429 A1 | 6/2013 | Ray, II |

FOREIGN PATENT DOCUMENTS

| CN | 1985814 A | 6/2007 |
| WO | 9944612 A1 | 9/1999 |

(Continued)

OTHER PUBLICATIONS

Sluka, K.A., et al. An experimental arthritis model in rats: The effects of NMDA and non-NMDA antagonists on aspartate and glutamate release in the dorsal horn. Neuroscience Letters, Limerick, IE. vol. 149, No. 1, Jan. 4, 1993.
(Continued)

*Primary Examiner* — T. Victor Oh
(74) *Attorney, Agent, or Firm* — King & Schickli, PLLC

(57) ABSTRACT

The present application relates to therapeutics and pharmaceutical compositions, their use and also methods for preventing post-traumatic osteoarthritis, early or late stage, using compounds which inhibit either, or both, AMPA and KA glutamate receptors (Glu Rs).

4 Claims, 23 Drawing Sheets

(51) Int. Cl.
    *A61K 9/00* (2006.01)
    *A61K 45/06* (2006.01)
(58) Field of Classification Search
    USPC .......................................................... 514/300
    See application file for complete search history.

(56)  References Cited

FOREIGN PATENT DOCUMENTS

| WO | 2004039247 | A2 | 5/2004 |
|---|---|---|---|
| WO | 2009021058 | A2 | 2/2009 |
| WO | 2010128977 | A1 | 11/2010 |
| WO | 2013059634 | A1 | 4/2013 |

OTHER PUBLICATIONS

Sluka, K.A., et al. Spinal cord amino acid release and content in an arthritis model: the effects of pretreatment with non-NMDA, NMDA, and NKI receptor antagonists. Brain Research, Elsevier, Amsterdam, NL. vol. 627, No. 1, Nov. 5, 1993.
Sluka, K.A., et al. Centrally administered non-NMDA but not NMDA receptor antagonists block peripheral knee joint inflammation. Pain, Elsevier Science Publishers, Amsterdam, NL. vol. 55, No. 2, Nov. 1993, pp. 217-225.
Jensen, et al., Tramadol versus Dextropropoxyphene in the Treatment of Osteoarthritis: A Short Term Double-Blind Study Drug Investigations, vol. 8, No. 4, 1994, pp. 211-218.
Bianchi, et al., Effects of tramadol on synovial fluid concentrations of substance P and interleukin-6 in patients with knee osteoarthritis: comparison with paracetamol. International Immunopharmacology vol. 3, No. 13-14m (2003) pp. 1901-1908.
Chernish, S.M., et al. A Comparison of Dextro-Propoxyphene Hydrochloride and Meperidine Hydrochloride. J. American Geriatrics Society, vol. 12, 1964, pp. 249-254.
Zhang, et al., The glutamatergic N-methyl-D-aspartate and non-N-methyl-D-aspartate receptors in the joint contribute to the induction, but not maintenance, of arthritic pain in rats. Neuroscience Letters, vol. 351, No. 3, 2003, pp. 177-180.
Piepoli, T., et al., Glutamate signaling in chondrocytes and the potential involvement of NMDA receptors in cell proliferation and inflammatory gene expression. Osteoarthritis and Cartilage, vol. 17, No. 8, 2009, pp. 1076-1083.
Parada-Turska, et al., Effect of glutamate receptor antagonists and antirheumatic drugs on proliferation of synoviocytes in vitro. European Journal of Pharmacology, vol. 535, No. 1-3, 2006, pp. 95-97.
Mason, D.J., et al., Ionotropic glutamate receptors are functional in human fibroblast-like synoviocytes and modulate IL-6 and MMp-2 expression. Bone, vol. 38, 2006, S33-S37, No. 73.
Szekely, et al., Apparent antinociceptive and anti-inflammatory effects of GYKI 52466. European Journal of Pharmacology vol. 336 (1997).
Lawand, et al., Glutamate receptors in the knee joint: a key role in peripheral sensitization. Society for Neuroscience abstract. vol. 24, 1998.
Martel-Pelletier, et al. Future therapeutics for osteoarthritis. Bone vol. 51 (2012) pp. 297-311.
Li, et al., Block of NMDA and non-NMDA receptor activation results in reduced background and evoked activity of central amygdala neurons in a model of arthritic pain. Pain, vol. 110 (1-2), 2004, pp. 112-122.
Written Opinion of the International Search Authority dated Aug. 29, 2014.
Combined Search and Examination Report dated Oct. 18, 2012 of the Patent Office of Great Britain.
Combined Search and Examination Report dated Dec. 11, 2013 of the Patent Office of Great Britain.
English machine translation of CN1985814(A).

A

B

| Glutamatergic signals | | AT SURGERY | | POST SURGERY | |
|---|---|---|---|---|---|
| | | MEDIAL | LATERAL | MEDIAL | LATERAL |
| EAAT1 | MIDDLE | ✓ | ✓ | ✓ | ✓ |
| | POSTERIOR | ✓ | - | ✓ | ✓ |
| EAAT1 ex9skip | MIDDLE | ✓ | ✓ | ✗ | ✗ |
| | POSTERIOR | ✗ | - | ✗ | ✓ |
| KA1 | MIDDLE | ✗ | ✗ | ✓ | ✓ |
| | POSTERIOR | ✗ | - | ✗ | ✓ |

Figure-6b.

SEQUENCE LISTING

<160> NUMBER OF SEQ ID NOS: 34

<210> SEQ ID NO 1
<211> LENGTH: 21
<212> TYPE: DNA
<213> ORGANISM: Homo sapiens

<400> SEQUENCE: 1
cgagttctgc tacaaatccc g                                             21

```
<210> SEQ ID NO 2
<211> LENGTH: 22
<212> TYPE: DNA
<213> ORGANISM: Homo sapiens

<400> SEQUENCE: 2
tgtccgtatg gcttcattga tg                                          22

<210> SEQ ID NO 3
<211> LENGTH: 27
<212> TYPE: DNA
<213> ORGANISM: Homo sapiens

<400> SEQUENCE: 3
ggaagtaagg aaaagaccag tgccctc                                     27

<210> SEQ ID NO 4
<211> LENGTH: 20
<212> TYPE: DNA
<213> ORGANISM: Homo sapiens

<400> SEQUENCE: 4
ttgccaaacc aaggcccccg                                             20

<210> SEQ ID NO 5
<211> LENGTH: 20
<212> TYPE: DNA
<213> ORGANISM: Homo sapiens

<400> SEQUENCE: 5
ggcaggaaaa gcgatacttg                                             20

<210> SEQ ID NO 6
<211> LENGTH: 20
<212> TYPE: DNA
<213> ORGANISM: Homo sapiens

<400> SEQUENCE: 6
ccaggttagc gagcatgtag                                             20

<210> SEQ ID NO 7
<211> LENGTH: 25
<212> TYPE: DNA
<213> ORGANISM: Homo sapiens

<400> SEQUENCE: 7
tgagcagtgt ctctctttca atgcc                                       25

<210> SEQ ID NO 8
<211> LENGTH: 25
<212> TYPE: DNA
<213> ORGANISM: Homo sapiens

<400> SEQUENCE: 8
tctctgagtt cgtctctggt gacaa                                       25

<210> SEQ ID NO 9
<211> LENGTH: 20
<212> TYPE: DNA
<213> ORGANISM: Homo sapiens

<400> SEQUENCE: 9
aaaccctggc gcttcgggac                                             20
```

<210> SEQ ID NO 10
<211> LENGTH: 20
<212> TYPE: DNA
<213> ORGANISM: Homo sapiens

<400> SEQUENCE: 10
gccactggct ggatcccacg                                               20

<210> SEQ ID NO 11
<211> LENGTH: 20
<212> TYPE: DNA
<213> ORGANISM: Homo sapiens

<400> SEQUENCE: 11
cgcttcggtg gccgcttcat                                               20

<210> SEQ ID NO 12
<211> LENGTH: 20
<212> TYPE: DNA
<213> ORGANISM: Homo sapiens

<400> SEQUENCE: 12
ccccgacctt ctcgaggcca                                               20

<210> SEQ ID NO 13
<211> LENGTH: 20
<212> TYPE: DNA
<213> ORGANISM: Homo sapiens

<400> SEQUENCE: 13
gaacttggga tggtgtcagc                                               20

<210> SEQ ID NO 14
<211> LENGTH: 20
<212> TYPE: DNA
<213> ORGANISM: Homo sapiens

<400> SEQUENCE: 14
agaaagcatg ggattggttg                                               20

<210> SEQ ID NO 15
<211> LENGTH: 20
<212> TYPE: DNA
<213> ORGANISM: Homo sapiens

<400> SEQUENCE: 15
gccctccgtc ccaccaggat                                               20

<210> SEQ ID NO 16
<211> LENGTH: 20
<212> TYPE: DNA
<213> ORGANISM: Homo sapiens

<400> SEQUENCE: 16
gacagcacct ggcagctggg                                               20

<210> SEQ ID NO 17
<211> LENGTH: 19
<212> TYPE: DNA
<213> ORGANISM: Homo sapiens

<400> SEQUENCE: 17
ccgggtcatc atcctttct                                              19

<210> SEQ ID NO 18
<211> LENGTH: 20
<212> TYPE: DNA
<213> ORGANISM: Homo sapiens

<400> SEQUENCE: 18
ttcttgccat tgatgagctg                                             20

<210> SEQ ID NO 19
<211> LENGTH: 20
<212> TYPE: DNA
<213> ORGANISM: Homo sapiens

<400> SEQUENCE: 19
ccggagagga gacttcacag                                             20

<210> SEQ ID NO 20
<211> LENGTH: 20
<212> TYPE: DNA
<213> ORGANISM: Homo sapiens

<400> SEQUENCE: 20
acagtgcatc atcgctgttc                                             20

<210> SEQ ID NO 21
<211> LENGTH: 19
<212> TYPE: DNA
<213> ORGANISM: Homo sapiens

<400> SEQUENCE: 21
accgctgtca ttgtgggta                                              19

<210> SEQ ID NO 22
<211> LENGTH: 20
<212> TYPE: DNA
<213> ORGANISM: Homo sapiens

<400> SEQUENCE: 22
gttccccagg aaaggagaag                                             20

<210> SEQ ID NO 23
<211> LENGTH: 21
<212> TYPE: DNA
<213> ORGANISM: Homo sapiens

<400> SEQUENCE: 23
cattaacatg gatgggactg c                                           21

<210> SEQ ID NO 24
<211> LENGTH: 18
<212> TYPE: DNA
<213> ORGANISM: Homo sapiens

<400> SEQUENCE: 24
cagctgtggc tgtgatgc                                               18

<210> SEQ ID NO 25
<211> LENGTH: 20
<212> TYPE: DNA
<213> ORGANISM: Homo sapiens

<400> SEQUENCE: 25

```
ctgccctcta tgaggctttg                                            20

<210> SEQ ID NO 26
<211> LENGTH: 20
<212> TYPE: DNA
<213> ORGANISM: Homo sapiens

<400> SEQUENCE: 26
tctcccagta cgttggtggt                                            20

<210> SEQ ID NO 27
<211> LENGTH: 20
<212> TYPE: DNA
<213> ORGANISM: Homo sapiens

<400> SEQUENCE: 27
tttggccaag aagaaagtgc                                            20

<210> SEQ ID NO 28
<211> LENGTH: 20
<212> TYPE: DNA
<213> ORGANISM: Homo sapiens

<400> SEQUENCE: 28
ccatcttccc tgatgcctta                                            20

<210> SEQ ID NO 29
<211> LENGTH: 18
<212> TYPE: DNA
<213> ORGANISM: Homo sapiens

<400> SEQUENCE: 29
cgctgtcatt gtgggaat                                              18

<210> SEQ ID NO 30
<211> LENGTH: 20
<212> TYPE: DNA
<213> ORGANISM: Homo sapiens

<400> SEQUENCE: 30
cacagcaatg atggtggtag                                            20

<210> SEQ ID NO 31
<211> LENGTH: 24
<212> TYPE: DNA
<213> ORGANISM: Homo sapiens

<400> SEQUENCE: 31
cggacaaatt attacaatca ggga                                       24

<210> SEQ ID NO 32
<211> LENGTH: 20
<212> TYPE: DNA
<213> ORGANISM: Homo sapiens

<400> SEQUENCE: 32
cgtgacaagt gctccacaat                                            20

<210> SEQ ID NO 33
<211> LENGTH: 26
<212> TYPE: DNA
<213> ORGANISM: Homo sapiens
```

```
<400> SEQUENCE: 33
gactgcagaa accatgtgtc agatcc                                        26

<210> SEQ ID NO 34
<211> LENGTH: 26
<212> TYPE: DNA
<213> ORGANISM: Homo sapiens

<400> SEQUENCE: 34
ggtgcagttg aagaagttca ggatcc                                        26
```

METHODS AND COMPOUNDS FOR PREVENTING OSTEOARTHRITIS

TECHNICAL FIELD

The present application relates to therapeutics and pharmaceutical compositions, their use and also methods for preventing post-traumatic osteoarthritis, early or late stage, using compounds which inhibit either, or both, (α-Amino-3-hydroxy-5-methyl-4-isoxazolepropionic acid) (AMPA) and kainate (KA) glutamate receptors (GluRs).

BACKGROUND

Osteoarthritis (OA) is a degenerative joint disease involving mechanical abnormalities such as joint degradation, both of the articular cartilage and bone, particularly subchondral bone. Bone changes often precede loss of cartilage. It can be caused by a variety of factors including hereditary, developmental, metabolic, and mechanical. In the latter instance, acute trauma such as damage to a joint or limb at one stage in an individual's life, can precipitate the condition at a later stage, in some instances much later i.e. 5-15 years later. Indeed, of the 95,000 anterior cruciate ligament reconstruction (ACL) operations and 38,000 arthroscopies to correct meniscal tears performed per year in the NHS, 50% of the treated patients proceed to early OA 5-15 years later. A proportion of these patients go on to need total joint replacement therapy, an extremely common and expensive procedure which is not successful in up to 20% patients undergoing knee replacement surgery. Similarly meniscal tears in the knee and tendon/ligament/disc damage in any joint predispose to joint degeneration which ultimately leads to osteoarthritis many years later.

Symptoms of OA may include joint pain, causing loss of movement, tenderness, stiffness, locking, and sometimes an effusion. Patients may also experience muscle spasm and contractions in the tendons. Occasionally, the joints may also be filled with fluid. As a result of decreased movement, adjacent muscles may atrophy, and ligaments may become more lax.

OA commonly affects the hands, feet, spine, and the large weight bearing joints, such as the hips and knees, although any joint in the body can be affected. As OA progresses, the affected joints change their shape, are stiff and painful, and usually feel better with gentle use but worse with excessive or prolonged use, thus distinguishing the disease from rheumatoid arthritis. In addition, and more profoundly, OA can be distinguished from RA on the basis that RA is an autoimmune, systemic disorder whereas OA does not involve a systemic immune response and is localised.

In smaller joints, such as the fingers, hard bony enlargements, called Heberden's nodes (on the distal interphalangeal joints) and/or Bouchard's nodes (on the proximal interphalangeal joints), may form, and though they are not necessarily painful, they do limit the movement of the fingers significantly. OA at the toes leads to the formation of bunions, rendering them red or swollen. Some people notice these physical changes before they experience any pain.

OA is the most common form of arthritis, and the leading cause of chronic disability in the United States. It affects nearly 27 million people in the United States and about 8 million people in the United Kingdom. Knee OA is one of the most common musculoskeletal diseases, affecting almost 251 million humans. Within this population, it is particularly concerning that over 30% of patients with acute anterior cruciate ligament (ACL) or meniscal injuries develop radiographic knee OA within 5 years post-injury. Joint trauma can lead to a spectrum of acute lesions, including osteochondral fractures, ligament or meniscus tears and damage to the articular cartilage. This is often associated with intra-articular bleeding and causes posttraumatic joint inflammation. Although the acute symptoms resolve and some of the lesions can be surgically repaired, joint injury triggers a chronic remodeling process in cartilage, bone and other joint tissues that initiates inflammatory and metabolic imbalance between anabolic and catabolic processes, tissue remodeling and biomechanical changes. The interactions between these biomechanical and biochemical changes propagate the path to degenerative joint disease that ultimately leads to joint failure.

There is therefore strong evidence implicating trauma with the likelihood of developing joint degeneration and OA. Indeed, this has led to the definition of a subset of the OA disease termed post traumatic osteoarthritis (PTOA) i.e. degenerative joint disease secondary to injury that may lead to OA years later. It is particularly prevalent in young and active individuals such as those involved in sport during which there is increased risk of sustaining such injury. It can therefore be defined as the presence of a normal joint prior to injury, structural damage at the time of injury and the joint not being compromised by systemic disease (Pickering, 1984). Joint trauma affects all joint tissues leading to physiological, biomechanical and biochemical changes that may progress toward joint degeneration and subsequent development of OA.

Treatment generally involves a combination of exercise, lifestyle modification, and analgesics. If pain becomes debilitating, joint replacement surgery may be necessary to improve the quality of life. Surgical intervention is sometimes recommended after joint injury to correct abnormal joint biomechanics, reducing the risk of secondary injuries, and ideally reducing the risk of OA. Unfortunately, surgical interventions (e.g. AU reconstruction, meniscectomy, meniscal replacement) do not restore normal joint biomechanics or prevent knee OA. Therefore, it is important to understand which of these patients will develop early-onset knee OA and if this onset of knee OA can be prevented or delayed. Whilst pain management and surgery are current options, currently there are no approved therapies to address post-traumatic arthritis and its prevention. There is a clear recognition of the risk of developing OA after joint trauma, and thus there is an obvious and urgent need to develop and implement strategies that prevent post-traumatic cartilage degradation.

The amino acid glutamate is the primary neurotransmitter in the vertebrate nervous system. However, as well as afferent and sympathetic nerve terminals, glutamate is released by numerous cells in the synovial joint including macrophages, lymphocytes, synoviocytes, osteoblasts and chondrocytes. Glutamate exerts its physiological effects by binding to various GluRs which are classified into two functionally distinct categories: ionotropic (iGluR) and metabotropic (mGluR).

The iGluRs act as glutamate-gated ion channels and are separated into three distinct sub-groups based upon their pharmacology: N-methyl-D-aspartate (NMDA), α-amino-3-hydroxy-5-methyl-4-isoxazolepropionic acid (AMPA) and kainate (KA). mGluRs are G protein-coupled receptors and can be divided into eight different sub-types (mGluR1-8) depending upon their structure and physiological activity. Glutamatergic signaling is regulated by five high affinity $Na^+$-dependent excitatory amino acid transporters (EAATs): EAAT1/GLAST, EAAT2/GLT-1, EAAT3/EAAC1, EAAT4, and EAAT5. In the synovial joint, functional GluRs and EAATs are expressed by synoviocytes, osteoblasts, osteoclasts, osteocytes, chondrocytes, tenocytes, macrophages and lymphocytes.

Our recent data revealed that human fibroblast-like synoviocytes (FLS) express functional GluRs that regulate FLS release of IL-6 and proMMP2 (27).

It is known that IL-6 concentrations are significantly increased in synovial tissue and fluid from active RA patients, and correlate with radiographic joint destruction. IL-6 promotes synovitis by inducing angiogenesis, infiltration of inflammatory cells and synovial hyperplasia, causes bone resorption by inducing osteoclast formation, and cartilage degeneration by stimulating matrix metalloproteinase (MMP) expression from synovial cells and chondrocytes. Elevated IL-6 levels in RA are produced mainly by FLS, with macrophages and chondrocytes producing significant, but lower levels. The important role of IL-6 in the pathology of RA is highlighted by IL-6$^{-/-}$ mouse studies in which reduced severity and delayed onset of arthritis are key outcomes. Treatment of RA patients with the anti-IL-6 receptor inhibitor tocilizumab significantly improves synovitis and radiographic changes, however, these significant benefits often come with a negative impact on host immunity, as seen in IL-6 deficient mice which are unable to clear bacterial infections and mount an effective T cell memory response.

Our recent published data (Flood et al 2007) revealed that activation of NMDA receptors decreases proMMP-2 release by human RA FLS. The noncompetitive NMDAR antagonist, MK801, significantly increased proMMP-2 release in RA but not normal FLS. However, the competitive NMDAR antagonist, D-AP5 and AMPA/KA receptor antagonists, CFM-2 and NBQX, did not affect MMP-2 expression by FLS. This work shows that activation of NMDA GluRs in RA FLS is dependent upon the nature of the antagonist.

Moreover, high glutamate concentrations increased IL-6 release by RA FLS via activation of KA receptors and this was inhibited by the AMPA/KA receptor antagonist NBQX, but not the AMPA receptor antagonist, CFM-2, nor the NMDA receptor inhibitors MK801 or D-AP5. This shows the effects on IL-6 are mediated via kainate receptors, not AMPA or NMDA receptors.

We have unexpectedly since discovered that specifically the subset of AMPA and KA (AMPA/KA) GluR inhibitors have therapeutic benefit in the prevention, prophylactically, of developing OA following trauma by administering to joints at, or about, the time of injury when there is no actual evidence of OA disease. Without wishing to be limited by any biological explanation we consider that increases in synovial fluid glutamate concentrations associated with disease at the time of injury, activates AMPA/KA GluRs that, in turn, lead to bone remodeling, mechano-responses, inflammation, pain and unexpectedly degeneration. It therefore follows that such GluRs may be therapeutically targeted at the time of injury or shortly thereafter to prevent the subsequent development of, mid to long term, degenerative joint disease leading to full-blown or late stage OA.

Prior to this work, GluR antagonists in the context of arthritis, more specifically OA, have been exclusively used systemically to alleviate pain in patients with established or advanced OA disease via the effects of the drugs upon neurotransmission, and/or inflammatory pain. The pain associated with OA usually occurs very late in the degenerative process, which is why OA is inherently difficult to treat as the symptoms come after the damage has occurred. In fact, the presence of pain is part of the clinical diagnosis of arthritis. This means that treatment with a drug to prevent pain would not be given at a time when treatment with a drug to prevent OA onset/progression would be given. In fact, patients at risk of developing OA (e.g. after ACL rupture, meniscal tear, rotator cuff injury, etc) do not, by definition, have arthritis (i.e. joint space narrowing on x-ray). All work hitherto has focused on treatment of pain in patients exhibiting disease, indeed using systemic administration, as the major effects of these drugs is via their effect upon the brain and spinal cord. For example, Martel-Pelletier (2012) reports that KA receptor antagonists have a role to play in nociception and that the ionotropic glutamate receptor iGluR5 antagonist LY545694 has been tested to treat central nervous system pain in knee OA but not as a disease modifying OA drug or in patients at risk of developing OA. Furthermore, Szekely et al (1997) reported that oral administration of GYKI 52466, a non-competitive antagonist of AMPA/KA receptors in rodent arthritis induced by intraplantar injection of 0.1 ml Freund adjuvant into the right hindpaw, had no effect on primary oedema on the right paw or the secondary, generalized inflammation-induced swelling of the left paw in the second phase of the chronic disease, but attenuated hyperalgesia and body weight loss, suggesting a central effect on chronic pain. This study showed no disease modifying effects and relates to central pain mechanisms.

In contrast we have identified that: i) the direct or targeted delivery of ii) a specific subset of GluR antagonists to iii) a damaged joint iv) at the time of trauma, or shortly thereafter when there is no evidence of joint OA, significantly prevents or reduces the likelihood of developing early stage OA i.e. degenerative joint disease leading to late stage OA (i.e. the effect of the antagonists is preventative rather than curative). The invention therefore has excellent potential for preventing OA disease from ever occurring as a result of joint injury. The invention is not concerned with treating or reversing OA disease once it has become established.

SUMMARY

Statements of Invention

In a first aspect of the invention there is provided an AMPA and/or a KA GluR antagonist that is formulated for administration to a joint for use in the prevention of, or reducing the likelihood of developing, post-traumatic osteoarthritis in the damaged joint.

In an alternative first aspect of the invention there is provided the use of an AMPA and/or a KA GluR antagonist in the manufacture of a medicament for administration to a joint to prevent, or reducing the likelihood of developing, post-traumatic osteoarthritis in the damaged joint.

Most preferably said joint is one damaged by trauma.

Reference herein to trauma refers to any event resulting in altered joint and tissue mechanics or inflammation, impairing the ability of the joint to withstand mechanical stress. For example, this includes but is not limited to, a high-force mechanical impact to the joint that can create immediate macro- and microdamage, which may compromise how tissues distribute joint loads and trigger tissue degradation. Additionally, or alternatively, low-energy injuries, including joint contusions, dislocations, tendinous and ligamentous injuries can also give rise to similar biomechanical changes and lead to pathology.

Typically, but not exclusively, this will include but is not limited to: damage to the articular cartilage surface; bone fractures; ligamentous and/or tendinous laxity or deficiency;

rupture of ligaments and/or menisci and/or tendons; lesions in the joint capsule and synovium; patellar dysfunction; compressive and/or shear damage to the articular cartilage.

In a preferred embodiment of the invention said disease is post-traumatic osteoarthritis (OA) either, early or late stage, in an individual who does not have rheumatoid arthritis (RA) or OA.

AMPA and/or KA GluR antagonists suitable for working the invention include, but are not limited to, 6-cyano-7-nitroquinoxaline-2,3-dione (CNQX), 6,7-dinitroquinoxaline-2,3-dione (DNQX), NS102—Selective of Kainate receptor over AMPA receptor, Kynurenic acid—endogenous ligand and Tezampanel; 2,3-dihydroxy-6-nitro-7-sulfamoyl-benzo[f]quinoxaline-2,3-dione (NBQX) and gamma-glutamylethylamide or 5-N-ethyl-glutamine (L-Theanine). Particularly preferred antagonists include 2,3-dihydroxy-6-nitro-7-sulfamoyl-benzo[f]quinoxaline-2,3-dione (NBQX), 6-cyano-7-nitroquinoxaline-2,3-dione (CNQX), Tezampanel and 2,3-dihydroxy-6-nitro-7-sulfamoyl-benzo[f]quinoxaline-2,3-dione (NBQX) and gamma-glutamylethylamide or 5-N-ethyl-glutamine (L-Theanine), 4-(8-Methyl-9H-1,3-dioxolo[4,5-h][2-,3]benzodiazepin-5-yl)-benzenamine (GYKI52466), 1-naphthyl acetyl sperm me (1-NAS) and 1-(4'-Aminophenyl)-3,5-dihydro-7,8-dimethoxy-4H-2,3-benzodiazepin-4-one (CFM-2). Other GluR antagonists known to those skilled in the art may also be used to work the invention. The activity of the afore antagonists, with respect to the AMPA and/or KA receptors can be summarised as follows.

| Antagonist | AMPA receptor antagonist | Kainate receptor antagonist |
| --- | --- | --- |
| CNQX | Yes | Yes |
| DNQX | Yes | Yes |
| NS-102 | Weak | Yes |
| Kynurenic acid* | Yes | Yes |
| Tezampanel | Yes | Yes |
| NBQX | Yes | Yes |
| L-Theanine* | Yes | Yes |
| GYKI52466 | Yes | Yes |
| 1-NAS | Yes | No |
| CFM-2 | Yes | No |
| ACET | No | Yes |

*Also antagonise NMDA receptors

In a further aspect of the invention there is provided a combination therapeutic comprising an AMPA and/or a KA GluR antagonist and at least one further therapeutic formulated for administration to a joint, ideally one damaged by trauma, for use in the prevention of post-traumatic osteoarthritis in said damaged joint.

More ideally still, said AMPA and/or KA GluR antagonist is ideally in the form of an injectable fluid or a topical formulation.

Therapeutics of the invention provided in solution disperse the pharmacologically active antagonist in the form of drops of a solution or a suspension. Pharmaceutical compositions in which the pharmacological active antagonist is in solution contain, in addition to this, a solvent and/or a stabiliser.

For topical application to the skin, the pharmacologically active antagonist may be made up into a cream, ointment, jelly, powder, solution or suspension etc. Cream or ointment formulations that may be used for the drug are conventional formulations well known in the art, for example, as described in standard text books of pharmaceutics such as the British Pharmacopoeia.

Formulation of the drug for joint application has the advantage of ensuring high drug concentrations at the trauma site with low systemic drug exposure, and thus reduced risk for any systemic adverse events. Moreover, it has been shown that systemic delivery of the drug does not achieve the requisite activity at the joint site and thus does not achieve the desired technical effect upon joint glutamate concentrations and thus prevention of joint degeneration and onset of disease.

In yet a further preferred embodiment of the invention, said antagonist is provided at a concentration between 1-100 mM, and more ideally between 2.5-25 mM including every 0.1 mM concentration there between. Most ideally, said antagonist is provided at a concentration selected from the group comprising: 2.5 mM; 5 mM, 7.5 mM, 10 mM, 12.5 mM, 15 mM 17.5 mM, 20 mM, 22.5 mM or 25 mM.

In yet a further preferred embodiment of the invention there is provided a method of preventing post-traumatic osteoarthritis in a damaged joint comprising administering to said joint at or about the time said joint is damaged an AMPA and/or a KA GluR antagonist formulated for administration to said joint.

In a preferred embodiment of the invention said disease is post-traumatic OA, early or late stage, in an individual who does not have rheumatoid arthritis (RA) or osteoarthritis (OA).

More preferably still, said method involves administering said antagonist at the following dosage: humans 0.03 mg/kg; rats 10 mg/kg and mice 30 mg/kg.

The invention herein described is for use in a mammal, more particularly a human, but the invention also has veterinary application and so use in relation to equine, porcine, canine, feline, ungulate, primate animals or, indeed, in relation to any load-bearing limbed animal that could go on to develop a degenerative joint or limb disorder such as OA.

In a preferred embodiment of any of the afore aspects of the invention said damaged joint includes, without limitation, any limb joint such as toes, ankle, knee, stifle, hip, fingers, wrist, elbow or shoulder, or any spinal joint including neck and any rib.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE DRAWINGS

The invention will now be described in greater detail with reference to the examples below and to the drawings in which.

DETAILED DESCRIPTION

Materials and Methods

Figure 1A:
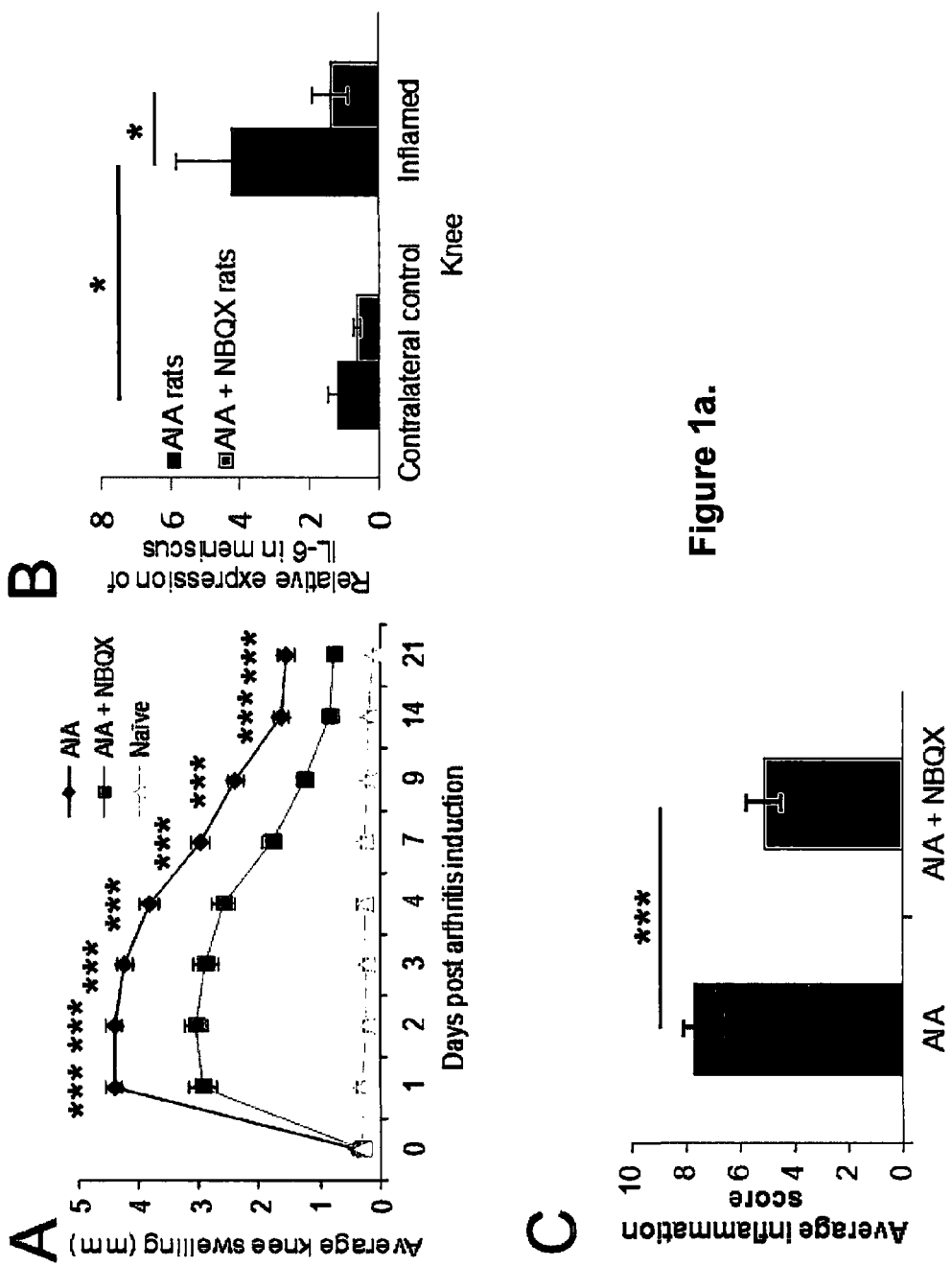
FIGS. 1a and b. Swelling, synovial inflammation and IL-6 mRNA expression in knees from naïve, AIA and AIA+NBQX rats. (A) Significantly less knee swelling was found in NBQX treated rats compared to AIA rats over 21 days (***P<0.001). (B) Significantly less IL-6 mRNA expression in the right inflamed knee was found in NBQX treated rats compared to AIA rats (*P<0.05). (C&D) Histopathological analysis of synovial inflammation in rat knees dissected on day 21. (C) NBQX treated rats had a significantly lower inflammation score compared to AIA rats (***P<0.001). (D) Normal synovial lining (SL) from naïve animals was 2-4 cells thick with adipose tissue (Ad) directly beneath, and normal articular surface (AS) consisted of a layer of smooth cartilage (Ca) over subchondral bone (Bo). Synovial hyperplasia (pannus formation (P)), exudate (E), infiltrate (I) and articular surface degradation apparent in AIA rats, was less severe in NBQX treated rats. MTP, medial tibial plateaux; LTP, lateral tibial plateaux; MFC, medial femoral condyle; LFC, lateral femoral condyle; M, meniscus. Boxes on large joint images indicate where images beneath were taken. Scale bars: (C-E) 1 mm, (F, H & J) 50 µm, (G, I & K) 100 µm.

Animals.

All procedures with animals were carried out in accordance with Home Office guidelines and following guidelines of the International Association for the Study of Pain. Male Lewis rats (for AIA) (~200 g) were obtained from Harlan (Oxfordshire, UK) and housed in conventional cages in groups of three. Rats received food and water ad libitum and were kept in a 12 hour light/dark cycle.

Arthritis Induction and Treatment Regime.

For AIA, after a 7 day settling in period, animals received a subcutaneous injection of methylated bovine serum albumin (mBSA; 0.5 mg/ml; Sigma, Poole, UK) emulsified with an equal volume of Freund's complete adjuvant (CFA; 0.25 mg *Mycobacterium tuberculosis*: Sigma) into the right flank. A second subcutaneous injection of the emulsion was administered in the left flank 7 days later. Fourteen days following the second injection (day 0), an intra-articular injection of mBSA (0.5 mg in 50 μl saline) was administered into the right knee of 15 rats to serve as the AIA group. Another 15 rats received an intra-articular injection of 0.5 mg mBSA mixed with 2.5 mM NBQX (Tocris, Bristol, UK) in 50 μl saline, into the right knee. These rats served as the NBQX treatment group. The NBQX concentration used was based upon studies investigating pain in rat carrageenan arthritis (1). Six control rats received no subcutaneous or intra-articular injections.

Knee Swelling.

Diameters of the inflamed (right) and non-inflamed (left) knees of all the rats were measured using a Mitutoyo® digital calliper (RS Components Ltd, Northants, UK) to quantify swelling. Measurements were taken on day 0 for a baseline reading (immediately prior to arthritis induction) and days 1, 2, 3, 4, 7, 9, 14 and 21 for AIA rats. Three readings were taken for each knee and the difference between the means of the inflamed and non-inflamed knee gave a value in millimeters of knee swelling.

IL-6 ELISA.

For AIA serum was collected from each rat via a tail bleed at baseline (day 0) and days 1, 2, 3, 7, 14 and 21. IL-6 levels were quantified in 6 rats from each group using a rat IL-6 Quantikine® kit (R&D Systems, Abingdon, UK) according to the manufacturer's instructions.

Histological Disease Assessment.

On day 21, 9 AIA, 9 NBQX and 3 control rats were culled and their knees dissected intact and fixed in 10% neutral buffered formalin solution (Sigma) for 2 days. Knees were decalcified in 10% EDTA (Fisher Scientific, Loughborough, UK) at 4° C., embedded in paraffin wax, sectioned (6 μm) in the coronal plane and stained with haematoxylin and eosin for synovial inflammation or toluidine blue/safranin-O for cartilage and bone scoring or retained for immunohistochemical analysis. Synovial inflammation and joint degradation were scored by two independent observers blinded to treatment group. An established scoring system was used to score synovial inflammation (3). Briefly, 3 parameters were scored: synovial hyperplasia (pannus formation) (0-3), synovial infiltrate (0-5) and synovial exudate (0-3), to give a maximum score of 11 per joint. Joint degradation was scored using a modified Mankin score (Table 1) consisting of: cartilage surface integrity (0-6), chondrocyte appearance (0-2), proteoglycan loss (0-4), tidemark integrity (0-2) and bone changes (0-3) to give a maximum score of 17 per joint quadrant (medial and lateral femoral condyles (MFC and LFC respectively) and medial and lateral tibial plateaux (MTP and LTP respectively)) totaling to a maximum of 68 per knee. In each knee, two representative sections ~500 μm apart were scored for joint degradation.

Footprint Scoring.

Hindlimb walking patterns were evaluated by footprint analysis on days 0, 1, 2, 3, 4, 7, 9, 14 and 21 as previously described (4). Six AIA, NBQX and control rats had their hind paws dipped in non-toxic paint and were then allowed to walk freely on a walkway (1 m long, 10 cm wide) lined with paper. Three sets of at least two stepping cycles per side (six sequential steps) were performed for each rat per experimental day. Three parameters were measured: limb rotation (angle between a line through the centre of the foot pad parallel to the walking direction and a line through the third digit), stride length (distance between feet of the same side) and stance width (distance between feet of the right and left stepping cycle).

Macroscopic Knee Analysis.

Prior to decalcification, whole rat knees were examined by radiography and MRI. Radiographs of both the inflamed and non-inflamed knees of 9 AIA, 9 NBQX and 3 control rats were obtained using a Kodak FX Pro in-vivo Imaging System (Advanced Molecular Vision, Grantham, UK), and the images analysed using Kodak Molecular Imaging software version 5 with the following parameters: 30 second exposure time at 35 kV, 4.96 F-stop, 71.4 mm FOV, 9.8 mm focal plane.

Both the inflamed and non-inflamed knee joints of 6 AIA and 6 NBQX rats were imaged using a high spatial resolution MRI scanning protocol at the Experimental MRI Centre (EMRIC, School of Biosciences, Cardiff University). Each pair of knees was embedded in 1% agarose (Promega) inside a 50 ml falcon tube prior to scanning. MRI was performed using a Bruker Biospin Advance 9.4T (400 mHz) MRI system equipped with a transmit-receive quadrature coil. The scanning acquisition parameters were as follows: echo time 1250 msec, repetition time 24 msec, field of view 640×280×280 mm; matrix 640×280×280; and flip angle 180°. Images were subsequently viewed and analysed in ParaVision 5.1 (Bruker) and Analyze 10.0 software Mayo Biomedical Imaging Resource, Rochester, Minn., USA).

Glutamate Receptor and IL-6 Messenger RNA (mRNA) Expression.

Menisci, patella, femoral shaft, femoral condyle and tibial plateaux were dissected from the inflamed and non-inflamed knees of 6 AIA and 6 NBQX rats culled on day 21. Human bone cores were taken from patients at the time of HTO surgery, immediately stored in dry ice and then placed in a −80° C. freezer. Total RNA was extracted with TRIzol (Invitrogen, Paisley, UK) as previously described (5), DNase treated (DNA-free™, Ambion, Warrington, UK), repurified and quantified by UV absorption. RNA (300 ng) primed with random primers (Promega, Southampton, UK) was reverse transcribed using SuperScript™ III reverse transcriptase (Invitrogen) and RNasin ribonuclease inhibitor (Promega), and RT-PCR performed (5). Primers were designed (Primer 3) to span introns of GluR, EAAT and IL-6 genes to discriminate genomic from complementary DNA (cDNA) amplification (Table 2) and PCR products cloned and sequenced to confirm correct amplification products. Rat or human brain and spleen cDNAs served as positive controls for GluR and IL-6 mRNA expression respectively. GluR and IL-6 expression changes were assessed by QRT-PCR (SYBR® Green JumpStart™ Taq ReadyMix™ without $MgCl_2$ (Sigma) with optimised primer and $MgCl_2$ concentrations, and thermocycling protocols, (Table 2) using an MX3000P PCR system and software (Stratagene). Standard curves (rat brain and spleen cDNA for GluR and IL-6 expression respectively) were repeated at least 3 times for each gene to ensure the efficiency of primers (90-110% efficiency and $R^2$ of 0.95) for relative quantification using the Pfaffl relative quantification method (6). NormFinder was used to identify the most stably expressed combination of housekeeping genes (GAPDH, HPRT1, eEF2 and YWHAZ) for normalisation of the target gene (7).

Meniscal Transection (MNX) Model.

We have established the meniscal transection (MNX) rat model of osteoarthritis. Surgery resection was performed wherein cutting through and removing part of the medial collateral ligament and then transecting the medial meniscus was performed under Home Office License. Surgery was performed under anaesthesia. Animals were then allowed to recover from surgery.

Using the MNX model, we tested the effects of NBQX injected directly into the knee joint. There were 5 groups of male Sprague-Dawley rats, 3 animals per group as follows:
MNX+sterile $H_2O$ (vehicle control)
MNX+2.5 mM NBQX
MNX+12.5 mM NBQX
MNX+25 mM NBQX
Naïve NBQX treated rats received two intra-articular injections, the first immediately after MNX surgery and the second 7 days later. A single dose of Temgesic was also given sub-cutaneously to relieve pain following surgery. Temgesic is effective for up to 12 hours but does not affect inflammation. Vehicle control rats received injections of sterile $H_2O$ delivered in the same way at the same times. Over 21 days, weight, knee swelling (digital calliper) and incapacitance (Linton incapacitance meter) were measured on days 0, 1, 2, 3, 7, 8, 10, 14 and 21. The Linton incapacitance meter measures the weight exerted on each back leg whilst the rat is stationary in a clear Perspex box. The difference in weight bearing can then be calculated between the left and right leg. All rats were euthanized on day 21 and the knee joints fixed in formalin for histology.

Non-Invasive Model of Post-Traumatic Knee Osteoarthritis.

We have established a non-invasive mouse model of post-traumatic knee joint degeneration due to ligament rupture. The non-invasive nature of this model means that large surgical influences on pain, inflammation do not mask early changes in arthritis onset and sham controls are not required.

Using custom built cups to hold the knee in flexion, loads (12N, 4 Hz, sine wave; ElectroForce® 3200, BOSE, USA) were applied to the right knees of 12-week-old C57Bl6 mice (n=10). Ligament rupture occurred between cycles 1-6, revealed by a continued increase in displacement following release of the applied compressive force during a loading cycle. Left knees served as unloaded controls. Immediately following ligament rupture, mice were given an intra-articular injection of 20 mM NBQX in to the right knee, whilst the control mice received an intra-articular injection of sterile $H_2O$ (vehicle control). A single dose of Temgesic was also given sub-cutaneously to relieve pain for up to 12 hours following loading.

Lameness scores were carried out every day for the first week and then every few days the following weeks to assess the welfare of the animals and the potential need for pain relief. Knee swelling was measured using digital callipers on days 0, 1, 2, 3, 7, 16 and 21. All mice were euthanized on day 21 and the knee joints fixed in formalin for histology.

Immunohistochemistry.

Animal Work:

GluRs and transporters were localised in sequential paraffin knee sections (9 AIA, 9 NBQX and 6 control knees) using antibodies to kainate (anti-KA1, 1:400 dilution), AMPA receptor-2 (anti-ionotropic glutamate receptor-2, 1:100, both Abcam, Cambridge, UK), GLAST (GLAST11-S, 1:100) and EAAC1 (EAAC11-A, 1:200, both Alpha Diagnostic International, Texas, USA). AMPAR2 was also localised in 6 MNX and 6 naïve rats. Sections, processed as for histology, were deparaffinised and rehydrated prior to antigen retrieval using 1 mg/mitrypsin (Sigma) for 20 minutes at 37° C. Endogenous peroxidase activity was blocked with 0.3% hydrogen peroxide (Sigma) for 30 minutes followed by 3 washes in 1×TBS/0.1% tween for 15 minutes each. Sections were treated with 10% normal blocking serum (Sigma) for 1 hour prior to overnight incubation at 4° C. with primary antibody, followed by 3 washes in 1×TBS/0.1% tween. Immunostaining was detected using the rabbit VECTASTAIN ELITE ABC horseradish peroxidase kit following the manufacturer's instructions (Vector Laboratories, Peterborough, UK). Sections were developed using nickel enhanced diaminobenzidine (DAB) (Vector Laboratories), counterstained in Mayer's haematoxylin (Fisher Scientific), rinsed in tap water, dehydrated, cleared in xylene and mounted. Slides were viewed on a Leica DMRB microscope. All incubations were at room temperature unless otherwise stated.

Human Work:

Consecutive sections from three human osteoarthritis medial tibial plateaux samples were immunostained for KA1, AMPAR2, EAAT1 (GLAST) and EAAT3 (EAAC1) using the same antibodies and techniques as detailed for the animal work above.

Statistical Analysis.

Data were tested for normal distribution and equal variances prior to parametric (one-way ANOVA with Fisher's a priori or Tukey-Kramer a posteriori post hoc tests) or non-parametric (Kruskal-Wallis with Mann-Whitney post hoc test) statistical tests using Minitab 16 software. All data are displayed as the mean±the standard error of the mean (SEM).

Results

Synovial Inflammation and IL-6 Expression is Reduced by NBQX Treatment.

Assessment of knee swelling in AIA rats revealed a severe acute inflammatory response during the first few days following induction (FIG. 1A), In AIA rats, mean knee swelling was 44 mm (±0.14 mm) on day 1, however in NBQX rats, the level was significantly less at only 2.95 mm (±0.23 mm), demonstrating a 33% reduction in peak knee swelling following NBQX treatment (P<0.001, Kruskal-Wallis test with Mann-Whitney post hoc test). This significant reduction in knee swelling in NBQX treated rats was seen at every time point throughout the 21 day experiment (P<0.001, Kruskal-Wallis test with Mann-Whitney post hoc test).

Serum IL-6 concentrations in AIR rats fell below the minimum detectable dose (21 pg/ml) of the IL-6 Quantikine® kit, therefore making them unquantifiable.

Figure 1B:
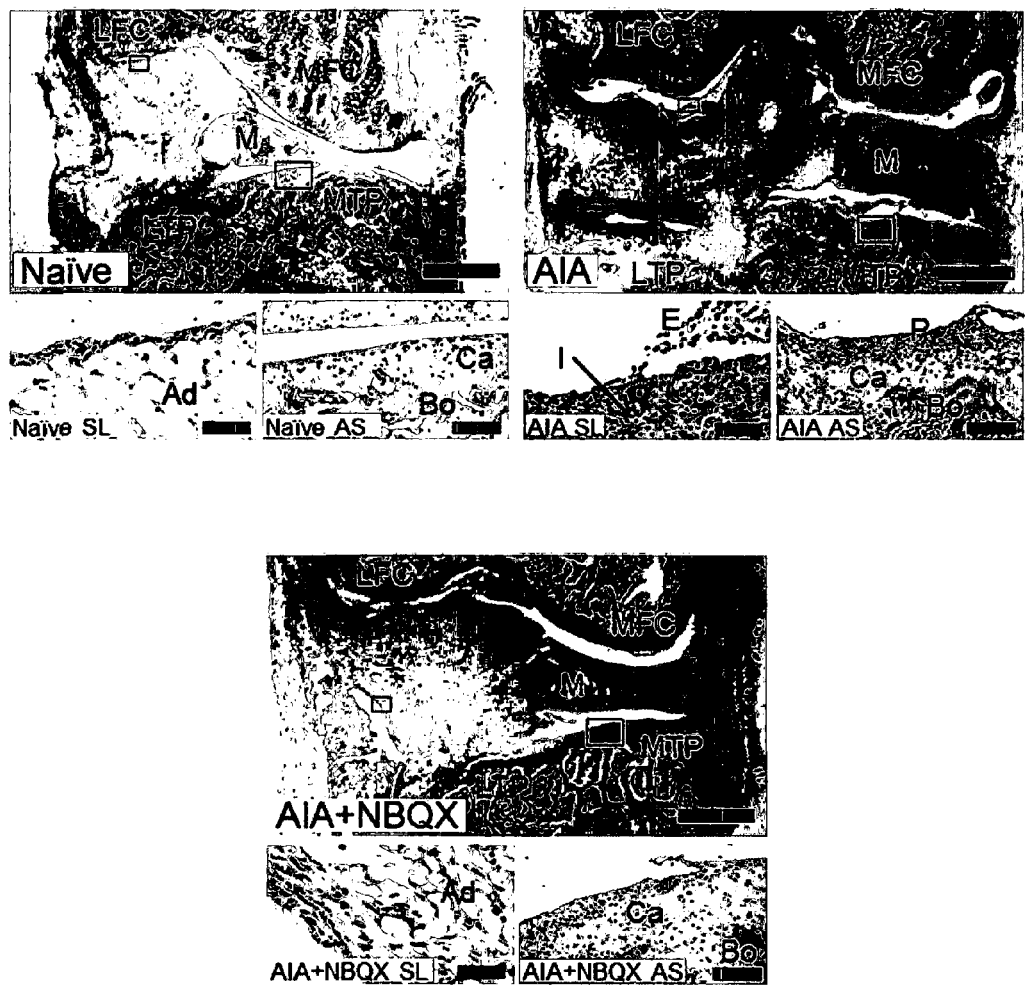

Investigation of IL-6 mRNA expression in AIA rat joint tissues from day 21 revealed that IL-6 was expressed at levels too low for quantification (although detectable) in the femoral condyle, femoral shaft, tibial plateaux and patella. In the meniscus, IL-6 relative expression levels were significantly lower (P<0.05, Kruskal-Wallis test with Mann Whitney post hoc test) in the inflamed knee of NBQX treated rats compared to AIA rats (FIG. 1B). The same pattern was also observed in the left non-inflamed knee, although not significant.

Histological examination of synovial inflammation in AIA, NBQX and control rat knees excised at day 21 revealed more severe synovial inflammation scores in AIA rats compared to NBQX treated rats (P<0.001, one-way ANOVA with Fisher's post hoc test) (FIG. 1C). Normal synovial lining from control animals was 2-4 cells thick with adipose tissue directly beneath, and normal articular surface consisted of a layer of smooth cartilage over subchondral bone (FIG. 1D). Synovial hyperplasia (pannus formation), exudate, infiltrate and articular surface degradation were apparent in AIA rats (FIG. 1D). This was significantly less severe in NBQX treated rats (FIG. 1D).

NBQX Treatment Restores Weight Bearing.

Figure 2A:
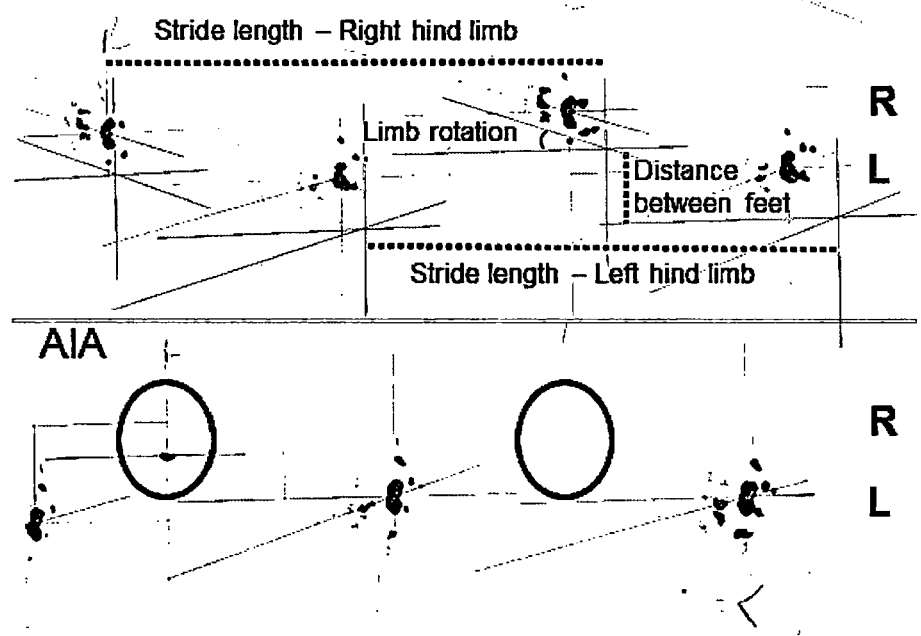
FIGS. 2a and b. Footprint analysis of naïve, AIA and AIA+NBQX rats. (A) Tracks of hindlimb footprints from the three experimental groups on day 1. AIA rats often lacked a right footprint (circled) whereas AIA+NBQX treated rats displayed a gait pattern resembling that of naïve animals. Measurements of degree of foot rotation, stride length and stance width are indicated in the top panel. (B-D) Analysis of foot rotation in the right inflamed limb (B), stance width (C) and stride length (D). Data are presented as group means+/−SEM. (B) AIA and AIA+NBQX treated rats have a significantly greater degree of foot rotation in the right limb compared to naïve rats. On days 1 and 2, AIA rats were unable to weight bear and therefore lack data points on the graph. Stance width was increased (C) and stride length decreased (D) in AIA and AIA+NBQX treated rats compared to naïve. *P<0.05, **P<0.001 AIA+NBQX compared to naïve, #P<0.05, ##P<0.001, AIA compared to naïve.
Figure 2A:
Figure 2B:
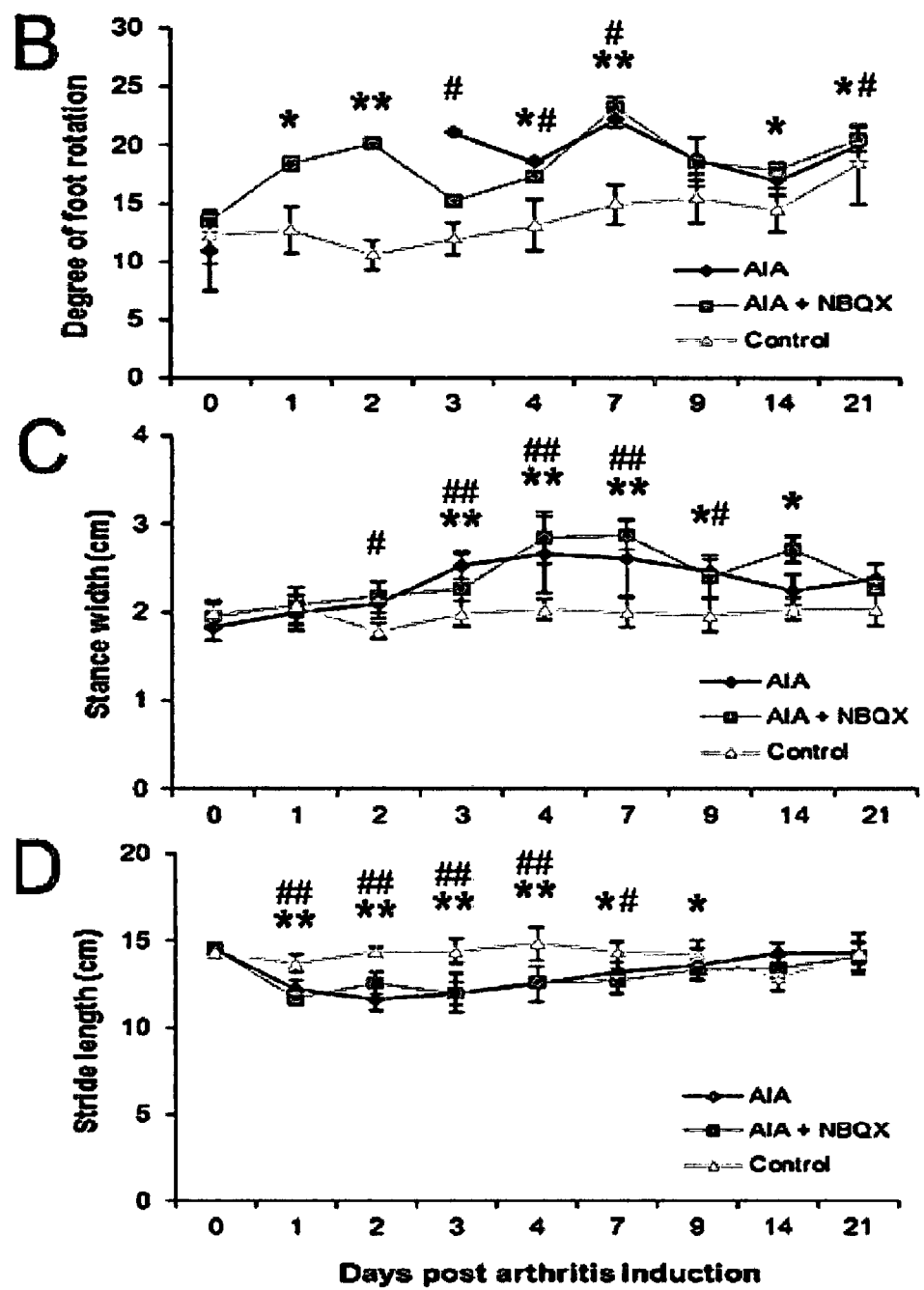

Footprint analysis revealed a striking difference between AIA and NBQX treated rats immediately after induction of arthritis. Whilst AIA rats had no measurable footprints on days 1 and 2 (FIGS. 2A & 2B), NBQX rats were able to weight bear on these days, displaying clear footprints, comparable to those seen in control rats. Analysis of gait parameters from footprints revealed walking abnormalities in both AIA and NBQX treated rats, with degree of foot rotation (FIG. 2B, P<0.05) and stance width (FIG. 2C, P<0.05) significantly greater and stride length (FIG. 2D, P<0.05) significantly shorter when compared to control rats (one way ANOVAs with Tukey-Kramer post hoc tests). By day 14, stride length had returned to normal in AIA and NBQX groups, and by day 21 stance width was normal in all groups.

Knee Joint Degradation is Reduced by NBQX Treatment.

Figure 3A:
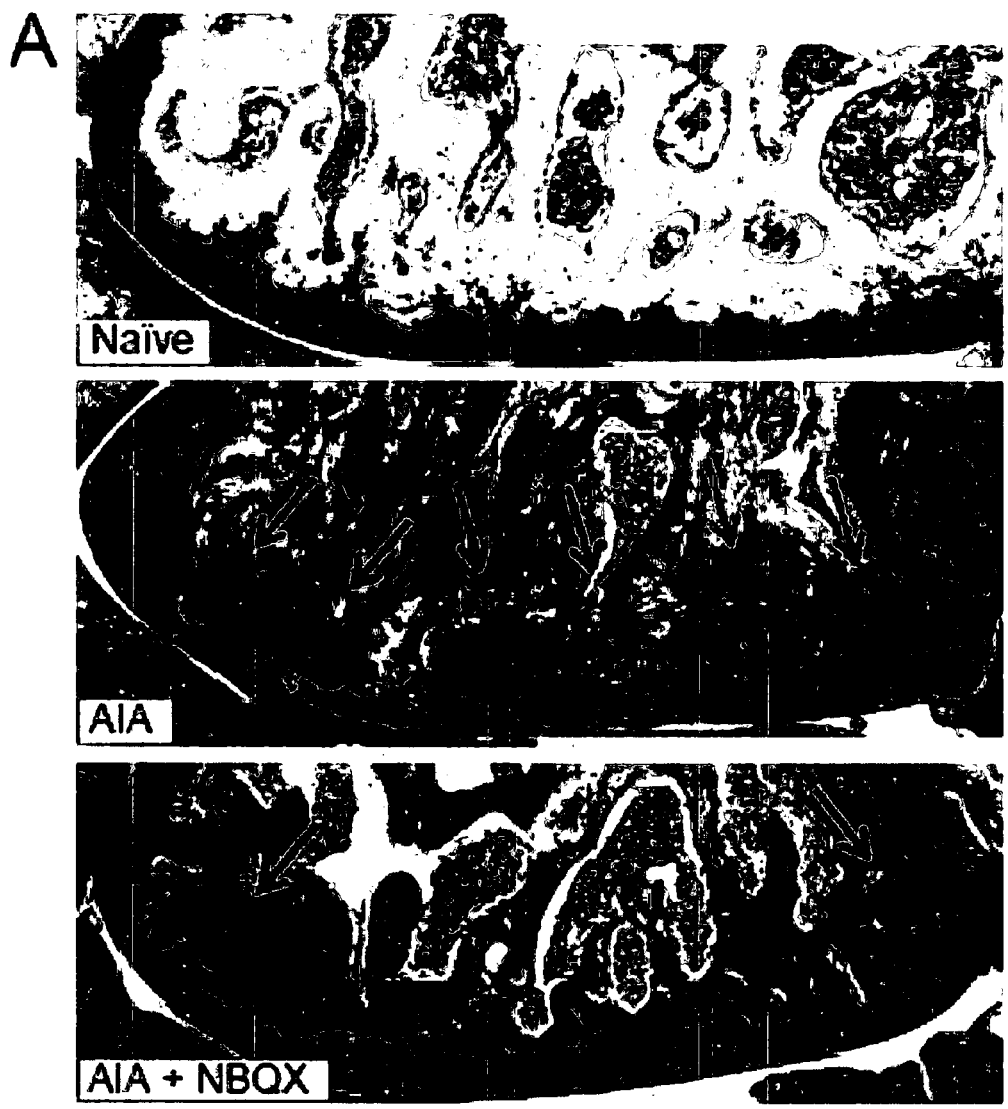
FIGS. 3a and b. Joint degradation and remodeling in naïve, AIA and AIA+NBQX rats dissected on day 21. (A) Toluidine blue staining of the lateral femoral condyle from a representative rat from each treatment group. (A&B) AIA+NBQX rats displayed less severe cartilage and bone pathology scores compared to AIA rats (P<0.001). (C) When divided into joint compartments, AIA+NBQX rats showed a significantly lower joint severity score compared to AIA rats in the femoral condyle (P<0.001). Abundant bone remodeling in AIA rats, indicated by toluidine blue staining (A), was significantly reduced in AIA+NBQX rats (P<0.001) (A&D (BC parameter)). (D) Chondrocyte appearance, proteoglycan loss and tidemark integrity scores were also lower in AIA+NBQX compared to AIA rats (P<0.01). MTP, medial tibial plateaux; LTP, lateral tibial plateaux; MFC, medial femoral condyle; LFC, lateral femoral condyle; CSI, cartilage surface integrity; CA, chondrocyte appearance; PL, proteoglycan loss; TI, tidemark integrity; BC, bone changes. *P<0.05, P<0.01, *P<0.001.
Figure 3B:
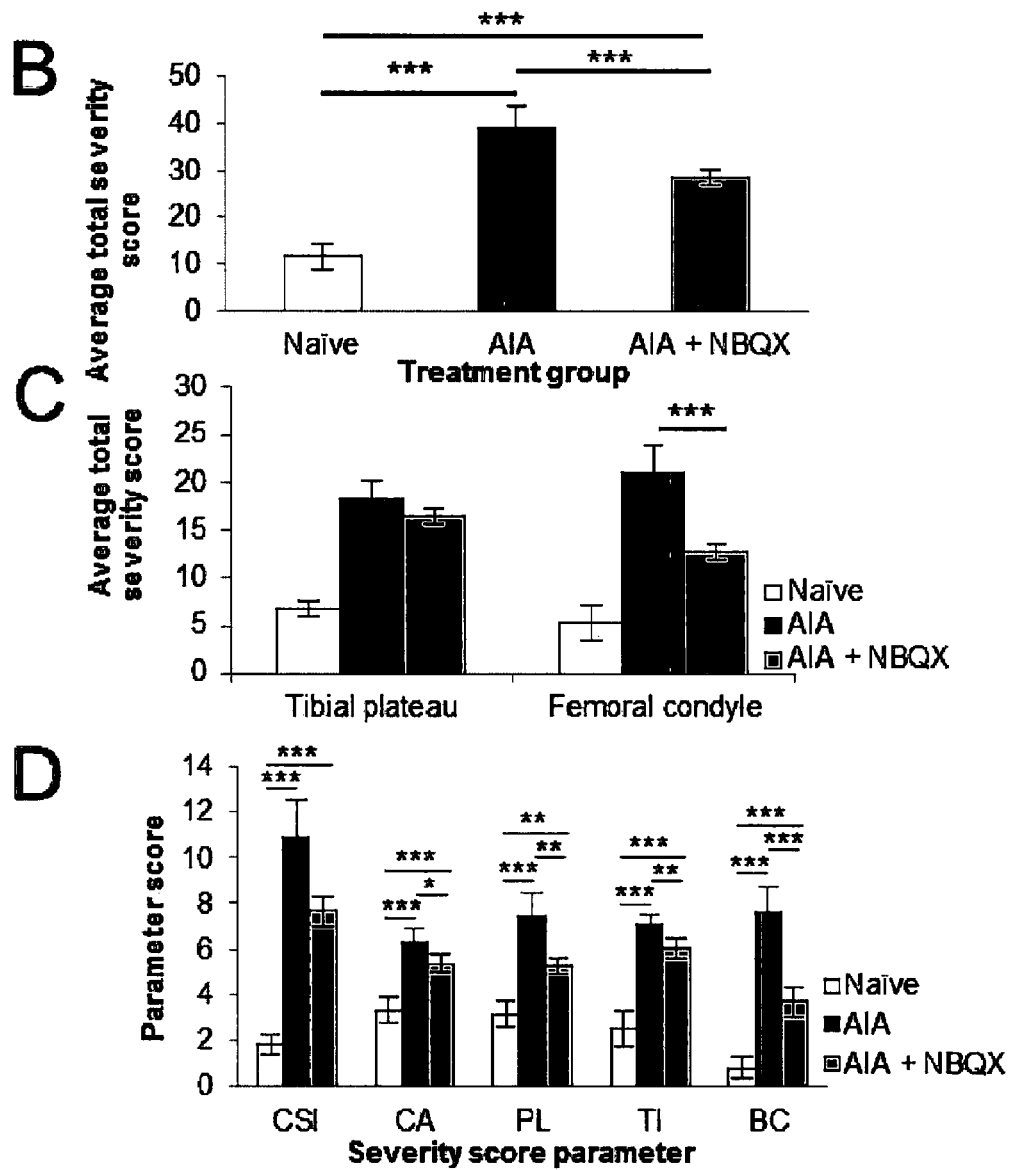

Histological assessment of joint degradation revealed significantly less cartilage and bone pathology in NBQX treated rats compared to AIA rats (FIG. 3). AIA rats displayed loss of cartilage and substantial boney changes underlying the articular cartilage (FIG. 3A). NBQX treated rats displayed a cartilage and bone phenotype resembling that seen in control animals, with minor remodeling at the outer edges (FIG. 3A). Average joint degeneration severity score was significantly reduced in NBQX treated rats compared with AIA rats (P<0.001, Kruskal-Wallis test with Mann Whitney post hoc test, FIG. 3B). Separating the joint into the 4 compartments (MTP, LTP, MFC and LFC) revealed significantly less joint degradation in the MFC and LFC in NBQX treated rats compared to AIA rats (P<0.01 and P<0.05 respectively, Kruskal-Wallis test with Mann Whitney post hoc test) (FIG. 3C). Dividing the severity score into the 5 parameters revealed that whilst NBQX treatment significantly lowered scores for chondrocyte appearance (P<0.05), proteoglycan loss (P<0.01) and tidemark integrity (P<0.01), the largest difference was observed in bone changes (P<0.001) compared with AIA (all Kruskal-Wallis test with Mann Whitney post hoc test) (FIG. 3D).

Figure 4A:
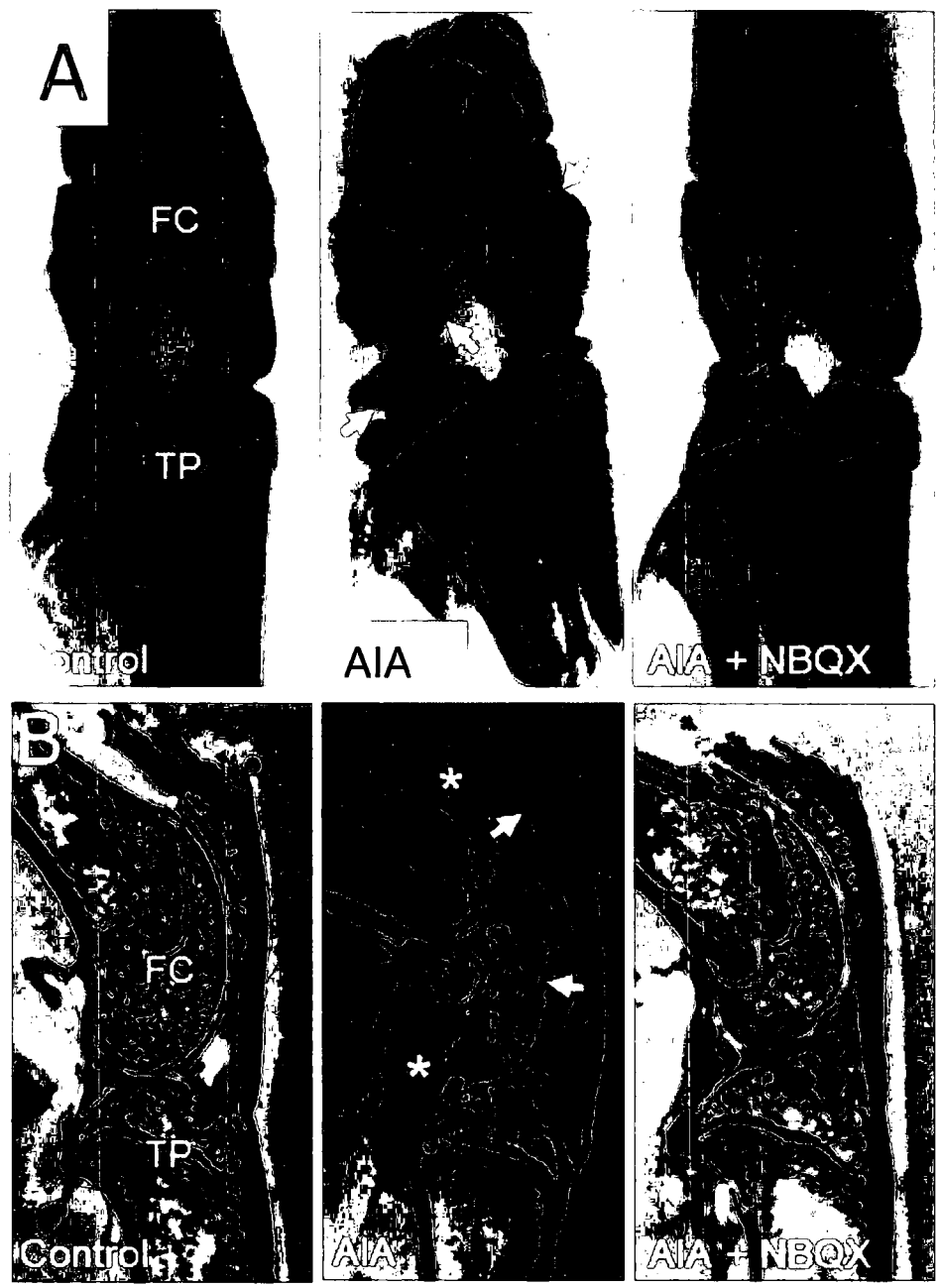
FIGS. 4a and b. Macroscopic joint pathology and bone phenotype mRNA expression in AIA and AIA+NBQX inflamed and contralateral control rat knees. (A) X-ray analysis revealed severe erosions in the tibial plateaux and femoral condyle in AIA rats (arrows). AIA+NBQX rats displayed a much smoother joint surface, resembling that seen in the contralateral control knee. (B) MRI analysis confirmed the erosions seen in x-rays (arrows), and also showed the presence of severe synovial inflammation (stars) in AIA rats. Synovial inflammation in AIA+NBQX knees was greatly reduced, as was joint erosion. FC, femoral condyle; TP, tibial plateaux. (C-G) Cathepsin K, collagen I, RANKL and the RANKL/OPG ratio mRNA expression levels were significantly increased in the AIA inflamed knee compared to the AIA and AIA+NBQX contralateral control knees. (C&D) Cathepsin K and collagen I mRNA expression was also significantly increased in inflamed AIA+NBQX knees compared to the AIA+NBQX contralateral control. (C) A significant reduction in cathepsin K mRNA expression was found in AIA+NBQX inflamed knees compared to AIA inflamed knees. (F) There were no differences in OPG expression. *P<0.05, P<0.01, *P<0.001.
Figure 4B:
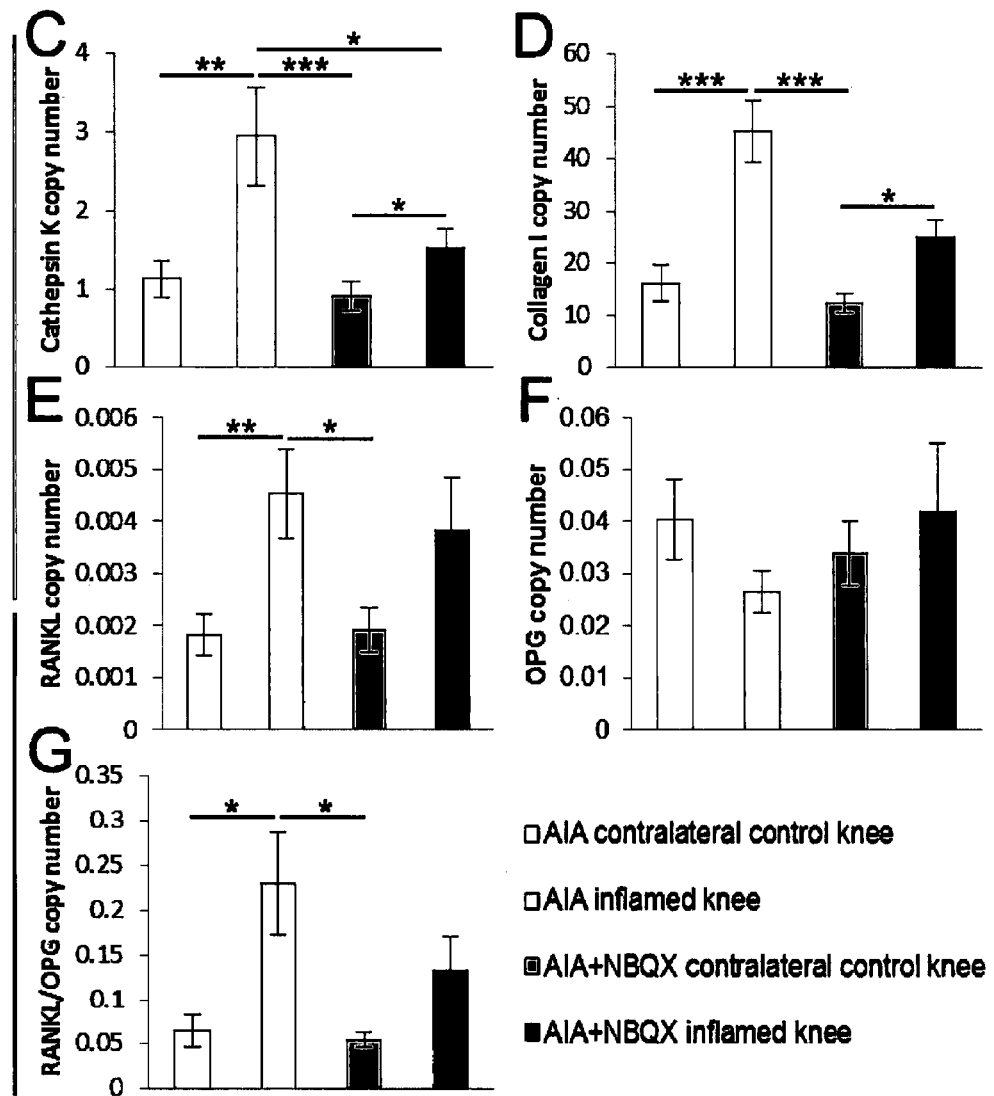

X-ray and MRI revealed joint erosions and synovial inflammation in AIA rats at day 21 (FIG. 4). Fewer joint erosions were seen in X-rays of NBQX treated rats which showed a more rounded, smooth articular surface, more closely resembling that of control animals (FIG. 4A). MRI of AIA rats at day 21 confirmed the severe erosions seen in x-rays, and also showed extensive synovial inflammation (FIG. 4B). MRI revealed that NBQX treatment greatly reduced synovial inflammation as well as joint erosion (FIG. 4B).

GluR Expression is Altered by NBQX Treatment.

Figure 5A:
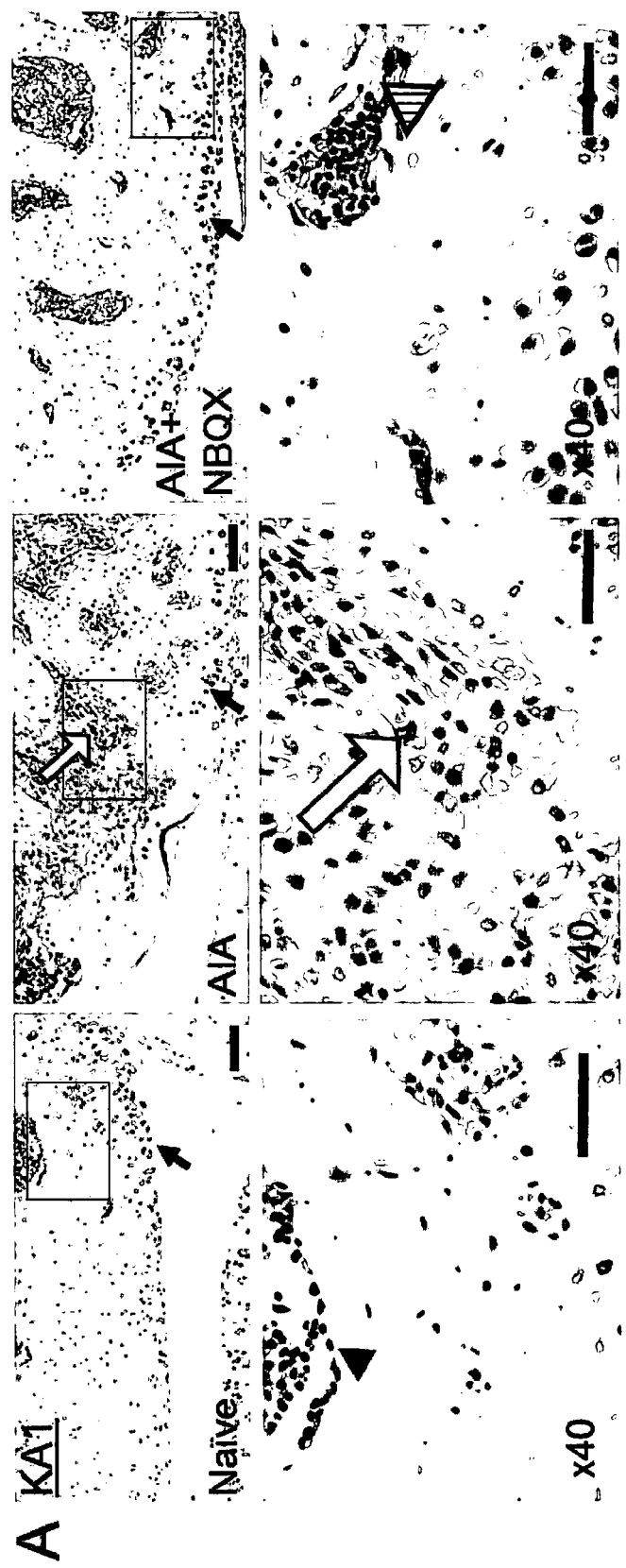
FIG. 5a-c. KA1 (A) and AMPAR2 (B) immunohistochemistry in the lateral femoral condyle from naïve, AIA and AIA+NBQX rats. Chondrocytes in naïve rats expressing KA1 and AMPAR2 (black arrows), appeared more numerous in AIA and AIA+NBQX. Neither proteins localised to osteocytes or mononuclear bone cells (black arrow heads, naïve ×40 images) in naïve rats, however, in AIA and AIA+NBQX rats, AMPAR2 was expressed in osteocytes, mainly in areas of bone remodeling (hollow arrow head, AIA ×40 image). In AIA rats, mononuclear bone cells and areas of bone remodeling stained intensely for KA1 and AMPAR2 (AIA ×40 images). AIA+NBQX treated rats showed less bone remodeling and subsequently less staining of both proteins (cross-hatched arrow heads, AIA+NBQX ×40 images). Abundant TRAP staining was found in AIA rats indicating the presence of more osteoclasts compared to the small amount of staining seen in naïve and AIA+NBQX rats (C). Consecutive sections showed expression of KA1 and AMPAR2 in TRAP positive osteoclasts in AIA rats (hollow arrows). Synovial lining cells expressed KA1 and AMPAR2 in all animals (data not shown). Black boxes are shown with a ×40 objective lens in smaller images. Corresponding negative controls (no primary antibody) and rabbit IgG controls were negative for KA1 and AMPAR2 (data not shown). Scale bars: Large images, 100 µm; small images; 50 µm.
Figure 5B:
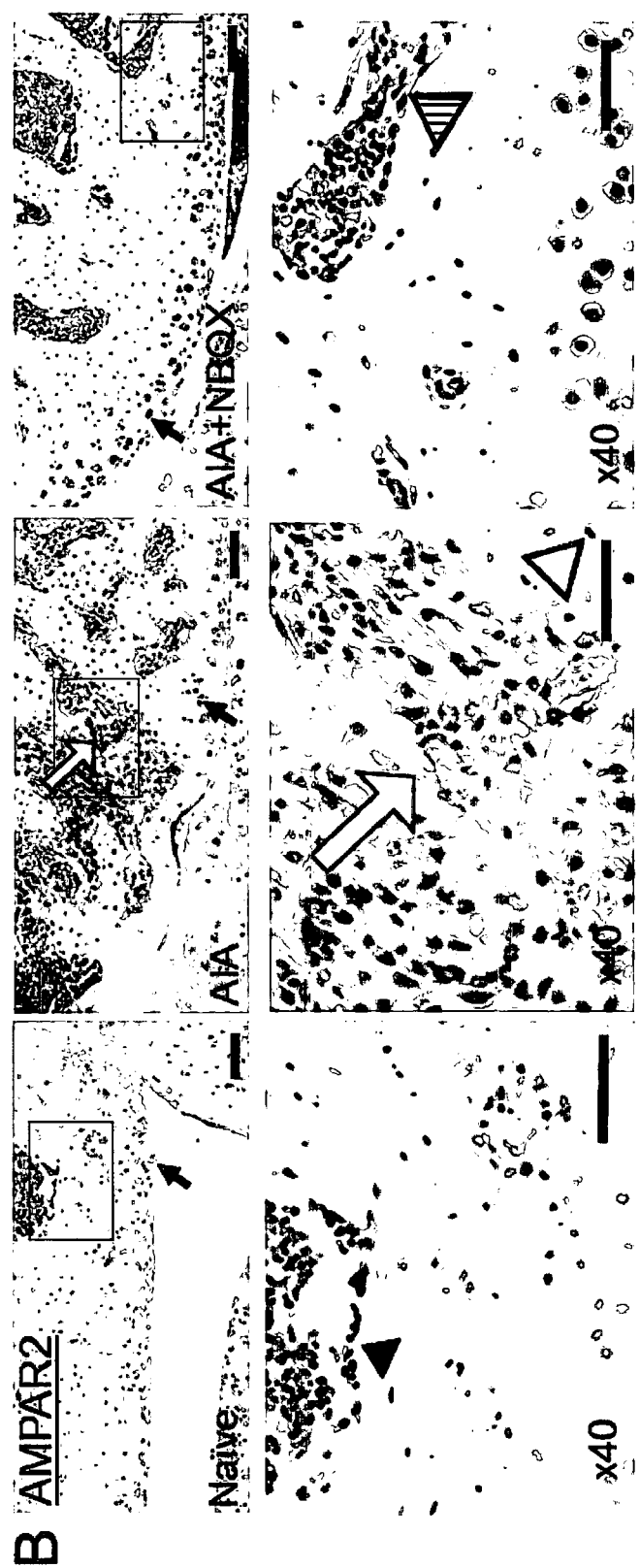
Figure 5C:

KA1 and AMPAR2 proteins were expressed in chondrocytes and synovial lining cells in all rats (not shown), and were abundant in remodeling bone in AIA (FIG. 5). Osteocytes and other mononuclear cells in the bone expressed AMPAR2 in areas of remodeling in AIA and AIA±NBQX (FIG. 5B), NBQX reduced the extent of remodeling, with an apparent reduction of GluR positive cells (FIG. 5), Neither AMPAR2 nor KA1 localised to mononuclear bone cells in naïve animals (FIG. 5). TRAP positive osteoclasts, abundant in AIA, co-expressed KA1 and AMPAR2 in consecutive sections and were less abundant in naïve and AIA+NBQX rats (FIG. 5).

GluR and EAAT Expression Responds to Mechanical Changes.

Figure 6A:
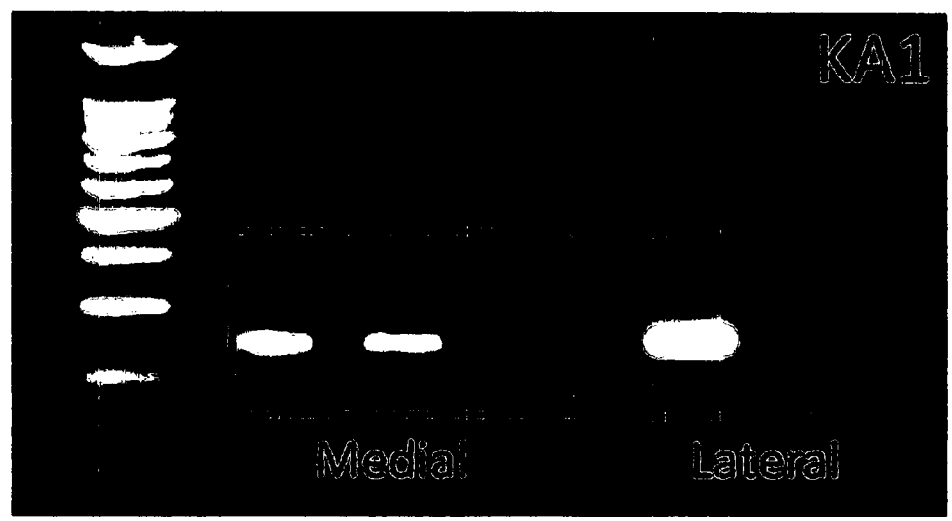
FIGS. 6a and b. GluR and EAAT mRNA expression following load changes across the joint after HTO surgery. (A) Kainate GluR mRNA expression was detected in medial (dark line) and lateral (light line) subchondral bone cores from an OA patient. (B) Kainate GluR and EAAT1ex9skip mRNA expression alters in bone cores taken at and 6 months post-HTO surgery in another OA patient, consistent with mechanical regulation of glutamate signaling in human bone.
Figure 6A:
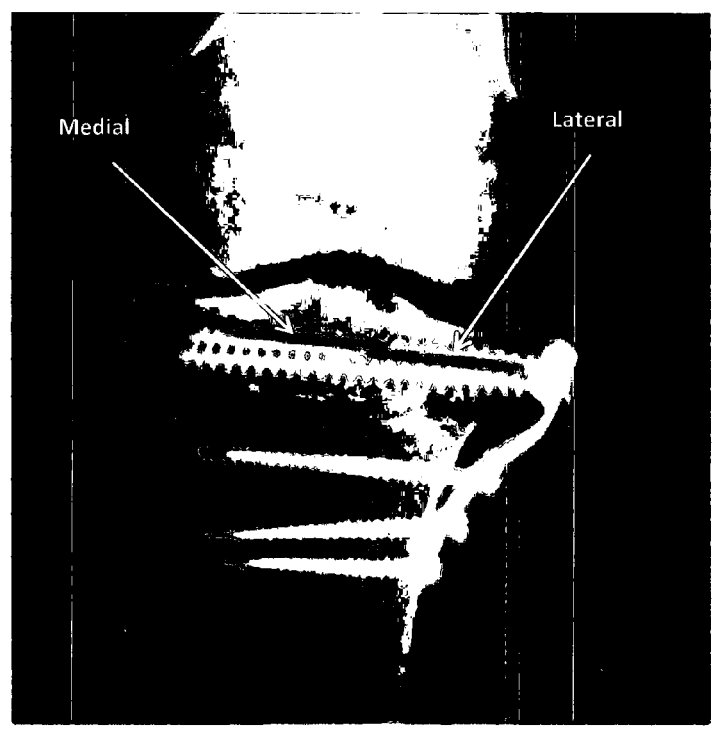
Figure 7:
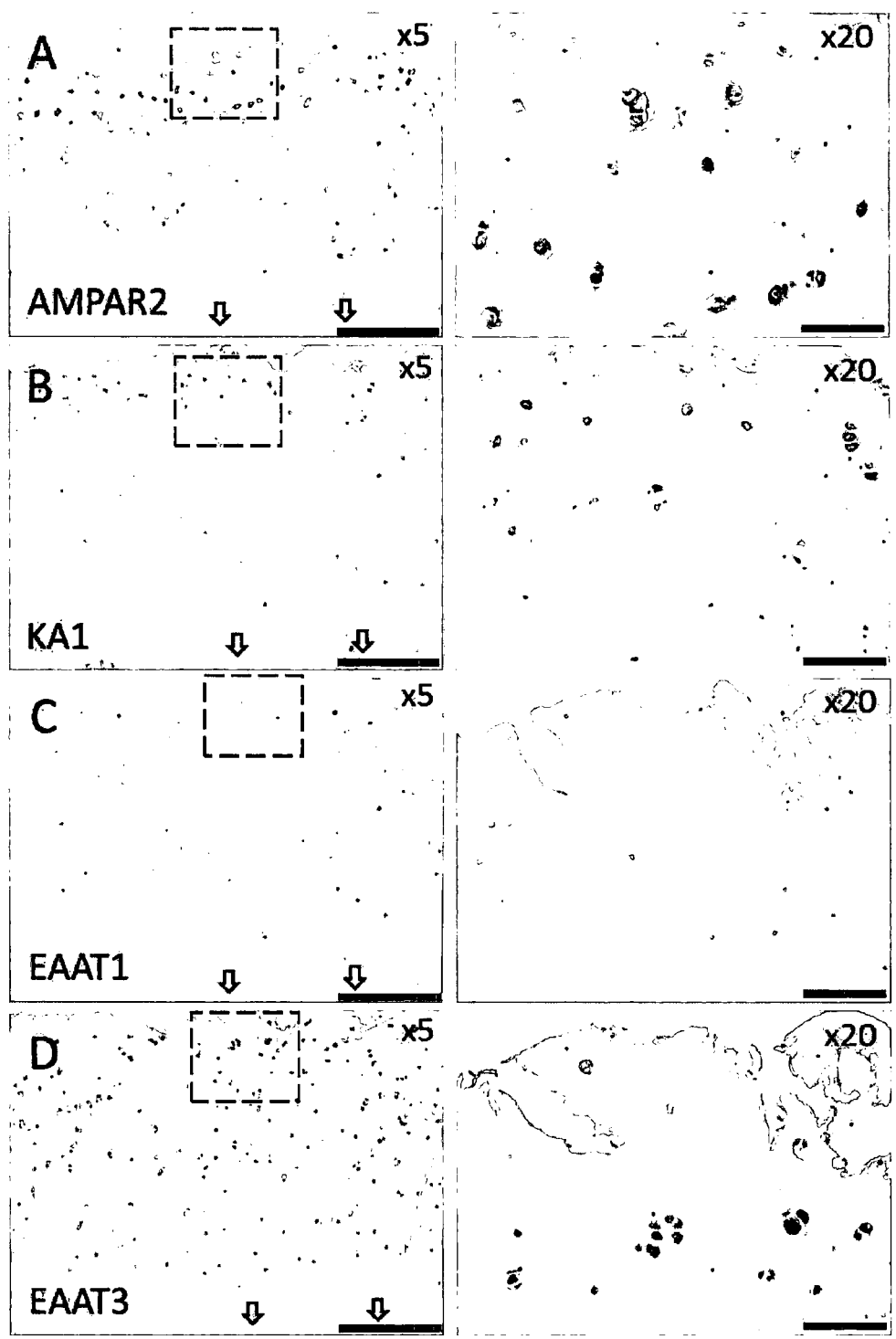
FIG. 7. GluR and transporter representative immunohistochemistry localisation in cartilage from the middle of the medial tibial plateaux (MTP) of a human OA sample (patient MS1). (A) Positive staining for AMPAR2 appeared cellular and was observed from the fibrillated cartilage surface down to the middle/deep zone interface, however, no staining was observed near the tidemark. Staining appeared strongest in the upper middle zone of the cartilage. (B) Positive staining for KA1 was observed from the surface down to the middle/deep zone interface, with no staining observed in the deep zone near the tidemark. Staining in surface chondrocytes appeared to be cellular. (C) EAAT1 was not localised to the cartilage of this patient, however, faint staining was observed in chondrocyte clones located at the surface of fibrillated cartilage in another patient (FIG. 8). (D) Positive staining for EAAT3 appeared cellular and was observed from the fibrillated cartilage surface down to the deep zone, however, no staining was observed next to the tidemark. Staining appeared strongest near the surface. Arrows indicate location of the tidemark. Boxes indicate where higher power image was taken. Scale bars: ×5 images, 500 µm; ×20 images, 100 µm.
Figure 8:
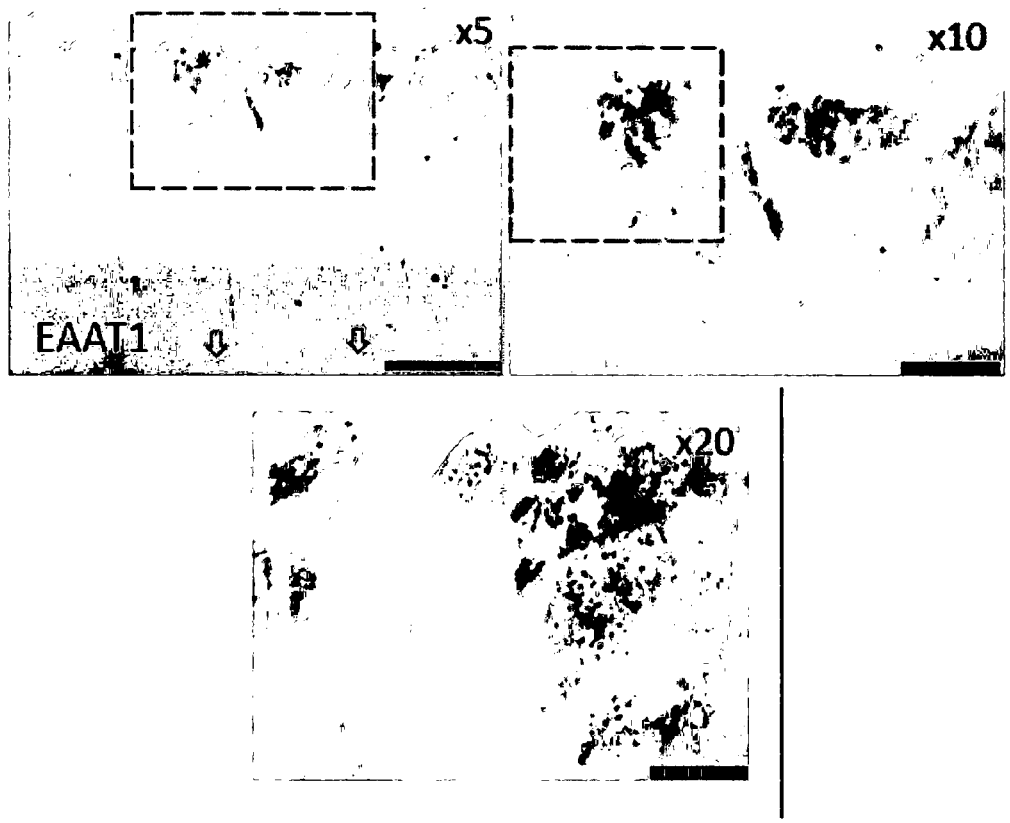
FIG. 8. EAAT1 expression near the surface of fibrillated cartilage from the middle of the MTP of an OA patient (different patient (JS2) to FIG. 7). This positive staining is seen surrounding chondrocyte clones. Staining appears to be pericellular. Arrows indicate location of the tidemark. Boxes indicate where higher power image was taken. Scale bars: ×5 images, 500 µm; ×10 images, 200 µm; ×20 images, 100 µm.
Figure 9:
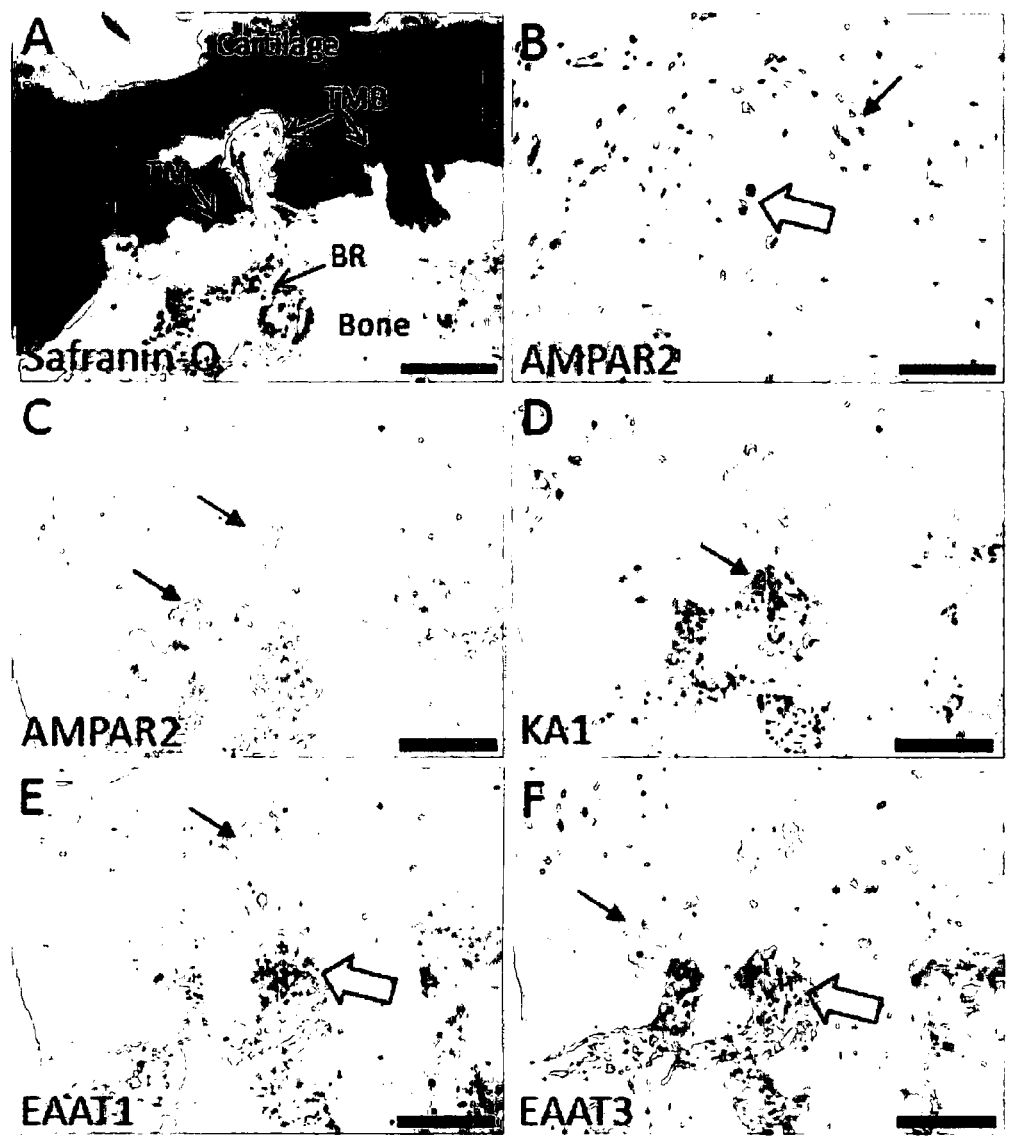
FIG. 9. GluR and transporter representative immunohistochemistry localisation in bone from the middle of the MTP of a human OA sample (patient MS1). A, C, D, E and F are all images from the same location in the MTP. (A) Safranin-O stain to show the architecture of the bone and cartilage. This area has remodeled and the tidemark (TM) is almost completely lost. Breaching of the tidemark (TMB) is also observed. This is likely to be vascular invasion but CD34 immunohistochemistry is required to confirm this. The bone is also undergoing remodeling (BR) as indicated by the dense appearance and cellularity. (C) AMPAR2 was localised to areas of remodeling, particularly to the TMB regions (arrows). This staining appeared to be pericellular. No staining was seen in bone lining cells from normal areas of bone (small arrow in B). Osteocyte AMPAR2 staining was occasionally observed, but only in small areas (large arrow in B). (D) KA1 localised to remodeling bone (arrow) and appeared to be cellular. No KA1 staining was seen in bone lining cells or osteocytes in normal bone. (E) EAAT1 staining was perivascular and observed in remodeling bone (large arrow) and TMB regions (small arrow). No positive staining was observed in normal bone. (F) EAAT3 localised to bone lining cells in normal bone (data not shown), remodeling bone (large arrow) and TMB regions (small arrow). Staining was cellular and also pericellular. Some osteocyte staining was observed (data not shown). Scale bars: A, C, D, E and F, 200 µm; B, 100 µm.
Figure 10:
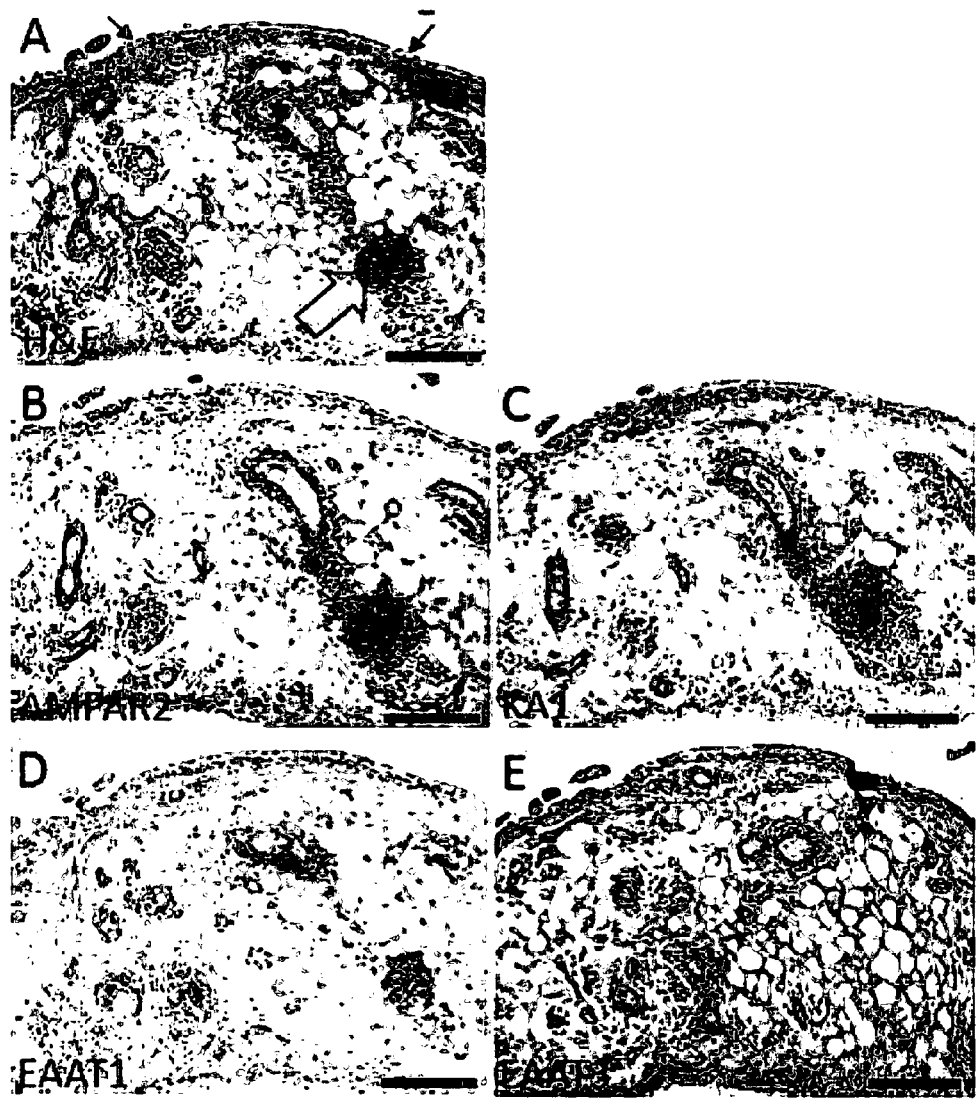
FIG. 10. GluR and transporter representative immunohistochemistry localisation in the synovium from a human OA sample (patient MS1). All images are from the same location in the synovial tissue. (A) Haematoxylin and eosin stain to show the architecture of the synovial tissue. Small arrows indicate the synovial lining and the star indicates a blood vessel. The large arrow highlights the presence of a perivascular lymphoid aggregate. This lymphoid aggregate, in combination with a thickened synovial lining, indicates inflammation of the synovial tissue, (B, C, D and E) AMPAR2, KA1, EAAT1 and EAAT3 are all localised to synoviocytes in the synovial lining and blood vessels. Scale bars: 200 µm.

KA1 expression differed between the medial and lateral side of the tibial plateaux where expression was present in the medial side but absent from the lateral side (FIG. 6A). In a different HTO patient, EAAT1ex9skip expression was lost following HTO surgery whilst KA1 expression was turned on (FIG. 6B).

GluR and Transporter Localisation in Cartilage, Bone and Synovium from the Middle of the Medial Tibial Plateaux (MTP) of Three Human OA Samples Positive staining for ionotrophic GluRs and transporters was seen in human OA cartilage: AMPAR2, EAAT3 and KA1 were observed from the fibrillated cartilage surface down to the middle/deep zone. EAAT1 expression was seen near the surface of fibrillated cartilage. Moreover, AMPAR2, KA1, EAAT1 and EAAT3 were localised to areas of bone remodeling in human OA tissue. Further, AMPAR2, KA1, EAAT1 and EAAT3 were all localised to synoviocytes in the synovial lining and blood vessels of human OA tissues. A comparison of Glu concentration in synovial fluid of joints of tissue taken from various species is shown in Table 3.

GluR Antagonism Reduces Knee Swelling and Pathology Following Joint Trauma

Figure 11:
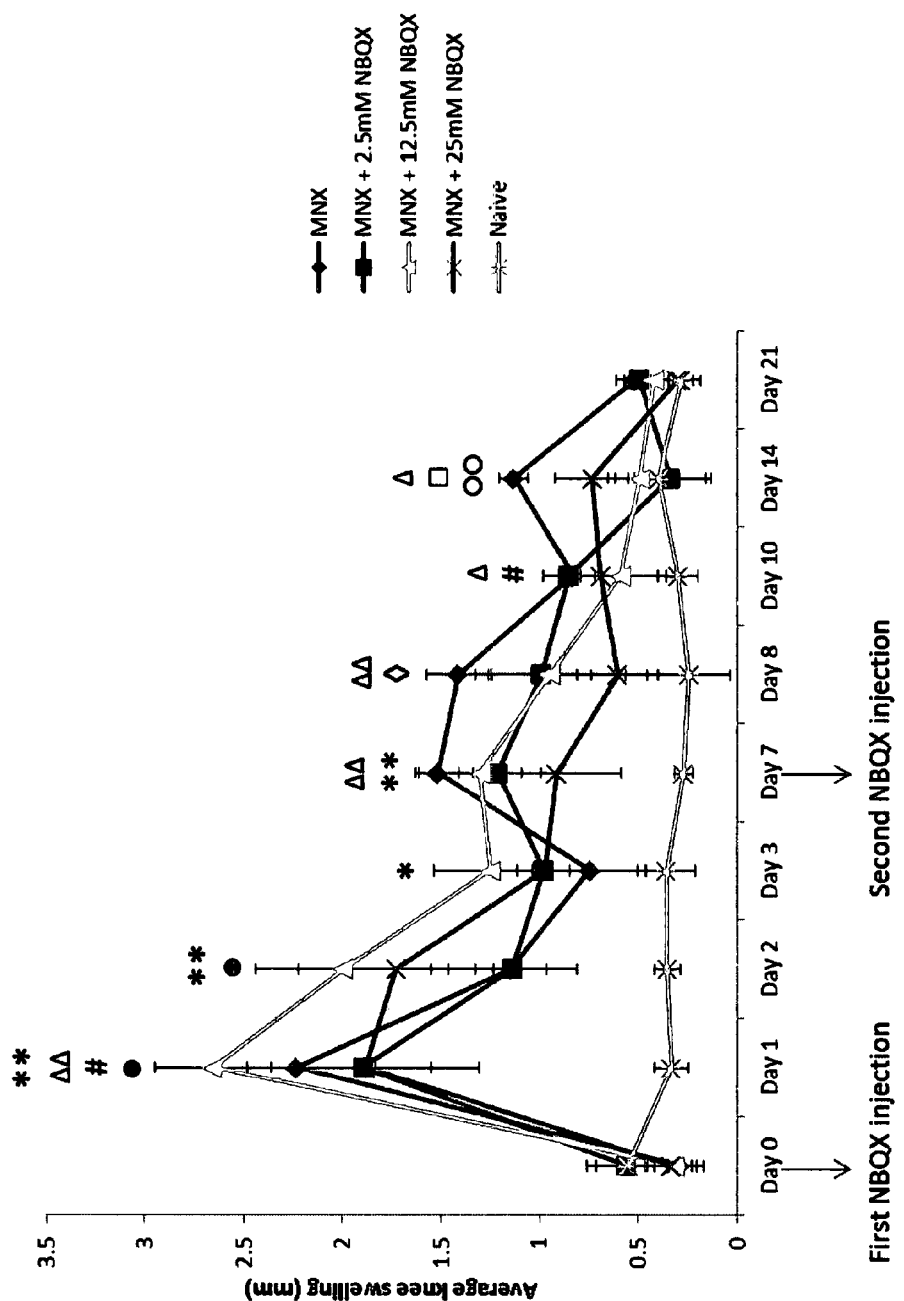
FIG. 11. Knee swelling following NBQX treatment in MNX rats. Average knee swelling is calculated as the right knee minus the left knee measurement. On day 8, vehicle control treated MNX rats had significantly greater knee swelling compared to naïve rats ($P<0.01$) and MNX rats treated with 25 mM NBQX ($P<0.05$). On day 14, vehicle control MNX rats had significantly greater knee swelling compared to naïve ($P<0.05$), 12.5 mM ($P<0.05$) and 2.5 mM ($P<0.01$) NBQX treated rats. MNX rats vs naïve, ΔΔ$P≤0.01$, Δ$P≤0.05$; MNX+2.5 mM NBQX vs naïve, #$P≤0.05$; MNX+12.5 mM NBQX, **$P≤0.01$, *$P≤0.05$; MNX+25 mM NBQX, ●$P≤0.05$. MNX vs MNX+25 mM NBQX, ◊$P0.05$; MNX vs MNX+12.5 mM NBQX, □$P≤0.05$; MNX vs 2.5 mM NBQX, ○○$P≤5.0.01$. One-way ANOVAs with Fisher's post hoc test.

Using the MNX model, rats undergoing surgery received intra-articular injections of varying concentrations of NBQX, immediately following surgery and a second injection 7 days later. Sterile water injections were performed in some mice to act as control. Over 21 days, weight, knee swelling (digital calliper) and incapacitance (Linton incapacitance meter) were measured on days 0, 1, 2, 3, 7, 8, 10, 14 and 21. All rats consistently put on weight throughout the experiment. The effects of NBQX on knee swelling were encouraging, particularly on days 8 and 14 following the second NBQX injection (FIG. 11). On day 8, vehicle control treated MNX rats had significantly greater knee swelling compared to naïve rats (P<0.01) and MNX rats treated with 25 mM NBQX (P<0.05). On day 14, vehicle control MNX rats had significantly greater knee swelling compared to naïve (P<0.05), 12.5 mM (P<0.05) and 2.5 mM (P<0.01) NBQX treated rats. This data supports our previous findings in the antigen induced arthritis (AIA) rat model and indicates that NBQX is having an anti-inflammatory effect on the knee joint following MNX surgery.

Figure 12:
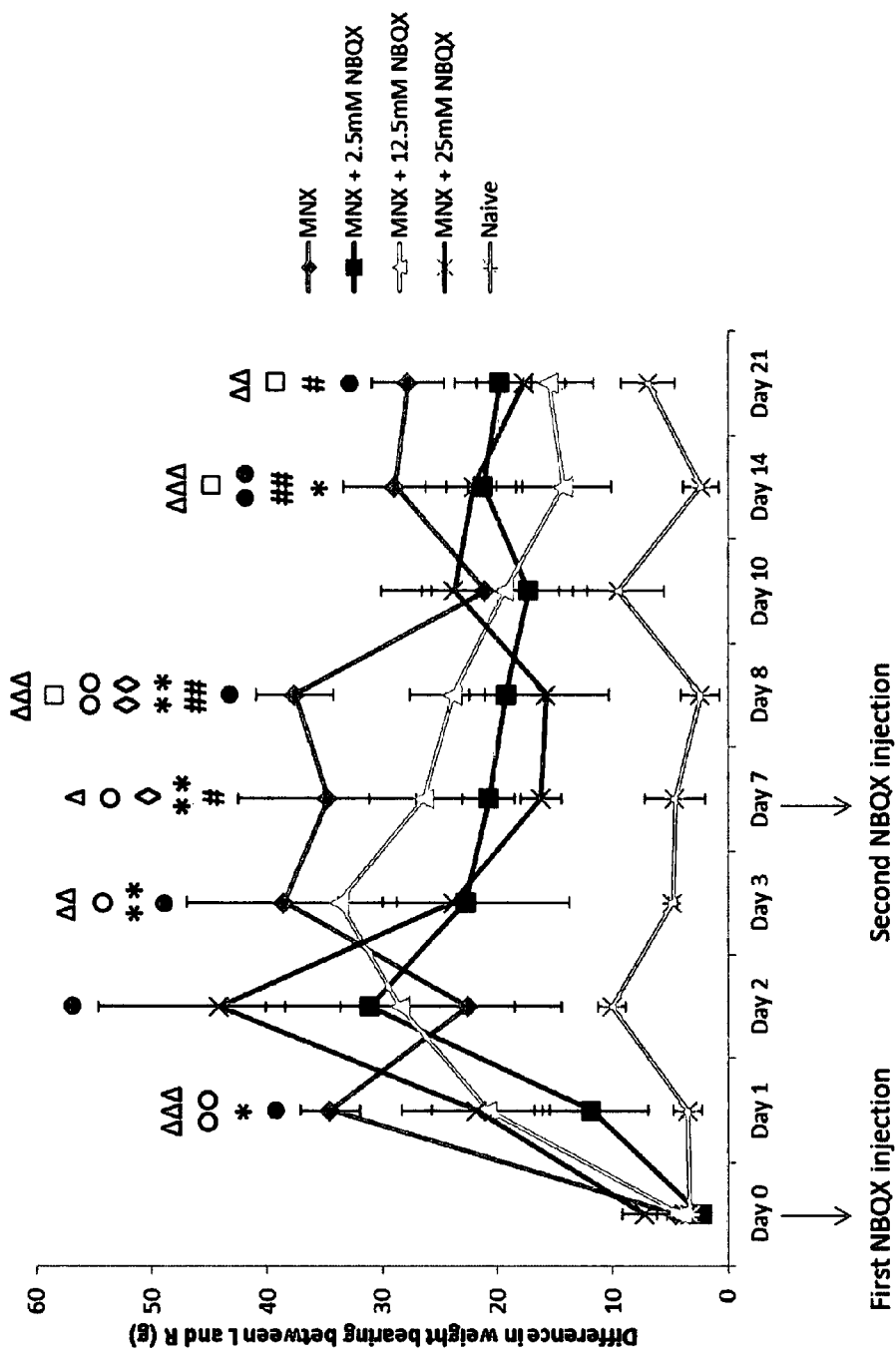
FIG. 12. Incapacitance testing following NBQX treatment in MNX rats. Difference in weight bearing between the left and right back legs of MNX rats following NBQX treatment. On day 8, immediately after the second NBQX injection, vehicle control treated MNX rats had a significantly greater difference in weight bearing between the left and right leg compared to naïve ($P<0.001$), 12.5 mM ($P<0.05$), 2.5 mM ($P<0.01$) and 25 mM ($P<0.01$) NBQX treated rats. MNX rats vs naïve, ΔΔΔ$P≤0.001$, ΔΔ$P≤0.01$, Δ$P≤0.05$; MNX+2.5 mM NBQX vs naïve, ##$P≤0.01$, #$P≤0.05$; MNX+12.5 mM NBQX vs naive, **$P≤0.01$, *$P≤0.05$; MNX+25 mM NBQX vs naive, ●●$P≤0.01$, ●$P≤0.05$. MNX vs MNX+25 mM NBQX, ◊◊$P≤0.01$, ◊$P≤0.05$; MNX vs MNX+12.5 mM NBQX, □$P≤0.05$; MNX vs 2.5 mM NBQX, ○○$P≤0.01$, ○$P≤0.05$. One-way ANOVAs with Fisher's post hoc test.

Incapacitance testing revealed that on day 8, immediately after the second NBQX injection, vehicle control treated MNX rats had a significantly greater difference in weight bearing between the left and right leg compared to naïve (P<0.001), 12.5 mM (P<0.05), 2.5 mM (P<0.01) and 25 mM (P<0.01) (FIG. 12). This data supports our previous findings that NBQX treatment provides pain relief in the days immediately following injection.

Figure 13:
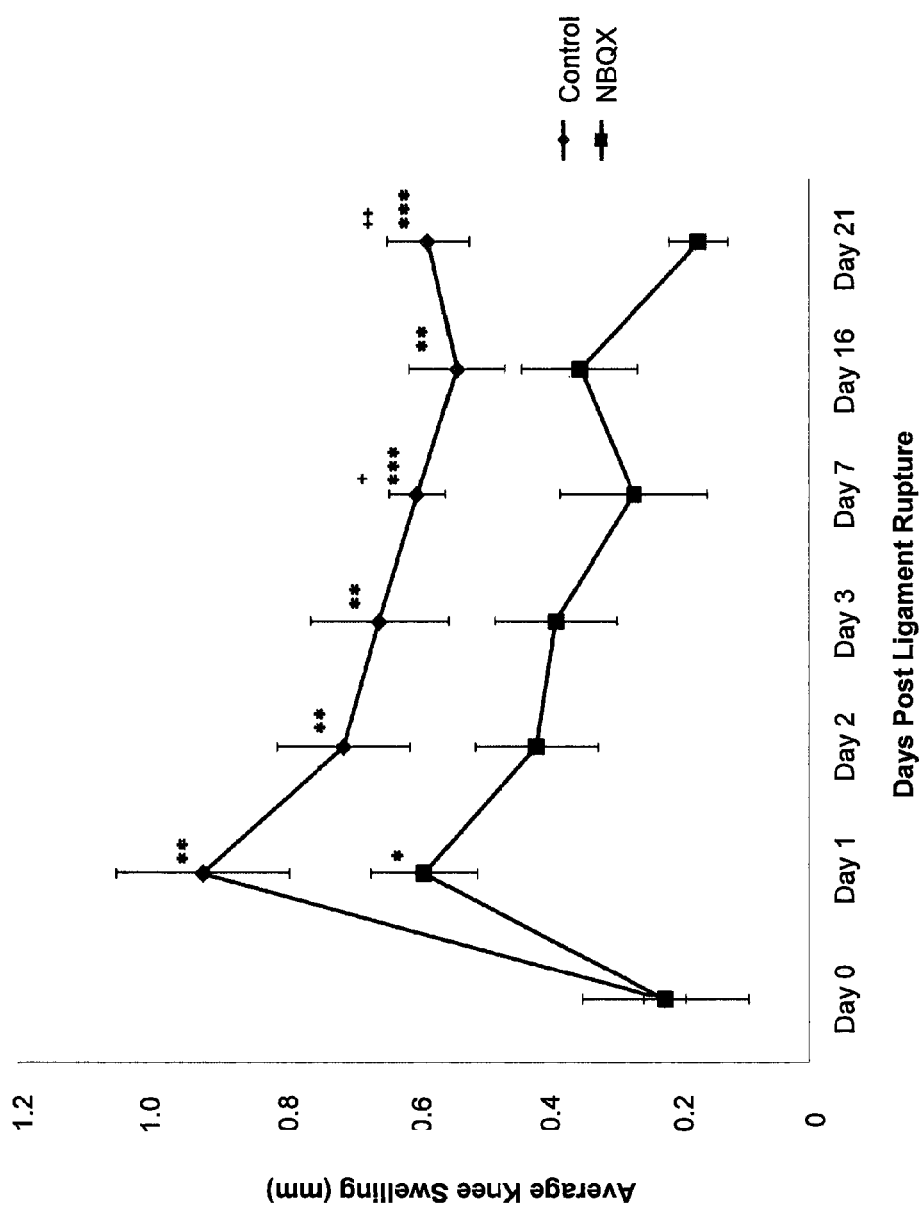
FIG. 13. Knee swelling following NBQX treatment in ligament ruptured mice. Significantly less knee swelling was found in NBQX treated mice compared to vehicle controls on days 7 ($P<0.05$) and 21 ($P<0.001$). From day 2, NBQX treated mice showed no significant difference in knee swelling compared to day 0 measurements. Vehicle treated mice had significantly greater knee swelling compared to day 0 at every time point. *vs day 0 NBQX, vs day 0 control, *vs day 0 control, + NBQX vs control, +++ NBQX vs control.

Using our non-invasive ligament rupture model, following trauma mice were given an intra-articular injection of 20 mM NBQX in the right knee. The left knee served as unloaded controls. Sterile water injections were performed in some mice to act as vehicle control. Knee swelling was measured using digital callipers on days 0, 1, 2, 3, 7, 16 and 21. All mice consistently put on weight throughout the experiment. Lameness scores were not severe enough to warrant extra doses of pain relief. The effects of NBQX on knee swelling were encouraging, with significantly less knee swelling in NBQX treated mice compared to vehicle controls on days 7 (P<0.05) and 21 (P<0.001) (FIG. 13). In addition, from day 2, NBQX treated mice showed no significant difference in knee swelling compared to day 0 measurements. In sharp contrast, vehicle treated mice had significantly greater knee swelling compared to day 0 at every time point, indicating that knee joint diameter never returned to control values without NBQX.

GluR and EAAT Expression Following Joint Trauma.

Right knees of 6 mice were loaded with a peak load of 9N, for 0.05 seconds for 40 cycles, with a baseline of 2N between each loading cycle. The rise and fall of loading cycle lasted 0.025 seconds. There were 3 loading episodes scheduled for the week, with the ACL rupturing on the $2^{nd}$ load (hence no $3^{rd}$ load required). Mice were culled two days after the second loading episode (after ACL rupture) and the knee joints dissected out. The left knees of the 6 mice served as unloaded controls.

Figure 14:
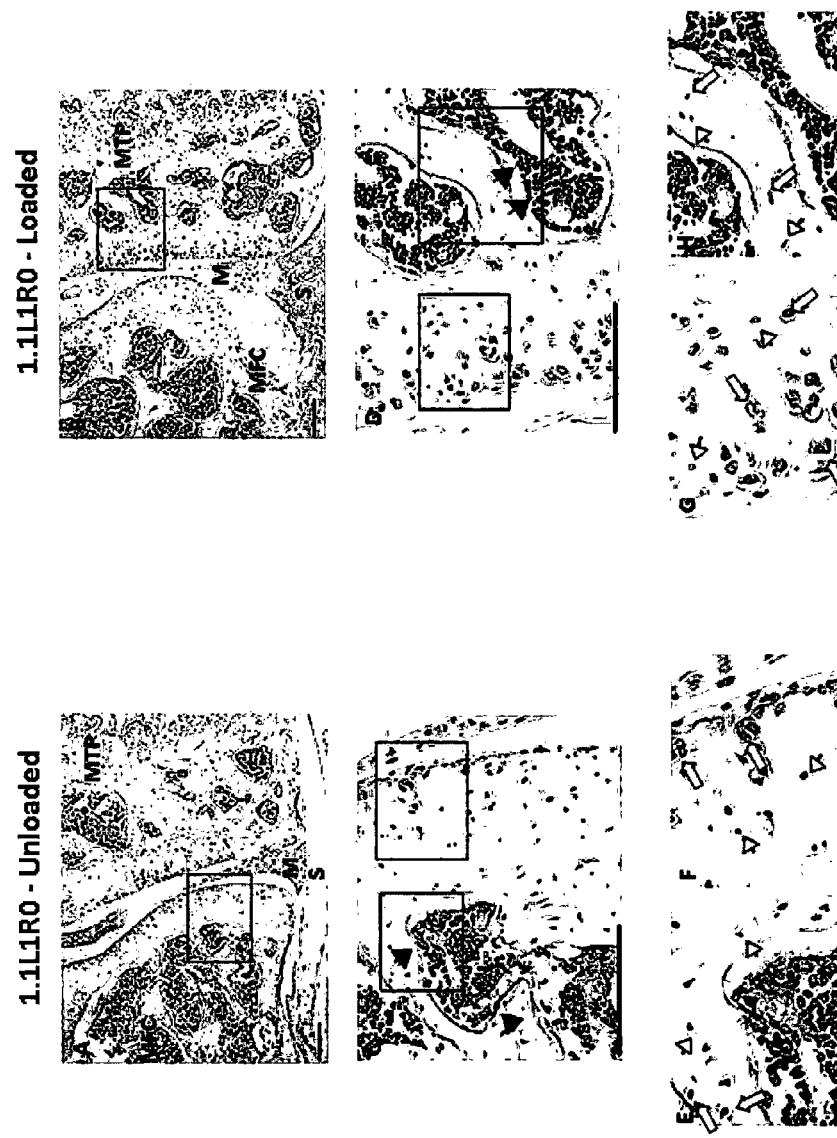
FIG. 14. EAAC1 immunohistochemistry images taken of the left (unloaded) and right (loaded) knee joints. 1.1L1R0=mouse ID. Images A and B taken at 10× magnification (100 µM scale bars), C and D at 40× magnification (100 µM scale bars) and E, F, G, H taken at 40× magnification (50 µM scale bars) on the medial side of the joint, (hollow arrow heads=unstained cells, hollow arrows=stained cells). (MTP=medial tibial plateau, MFC=medial femoral condyle, M=meniscus, S=Synovium). There is significant staining in the bone lining cells (black arrow heads C and D) on both the left and right legs. There is also staining (hollow arrows) throughout the cartilage in the chondrocytes and in between the bone matrix in the osteocytes. Although EAAC1 is a strong antibody, there is some chondrocytes and osteocytes that did not stain (hollow arrow heads). There is however a significant amount of staining in the synovium in the right leg compared to the left leg.
Figure 15:
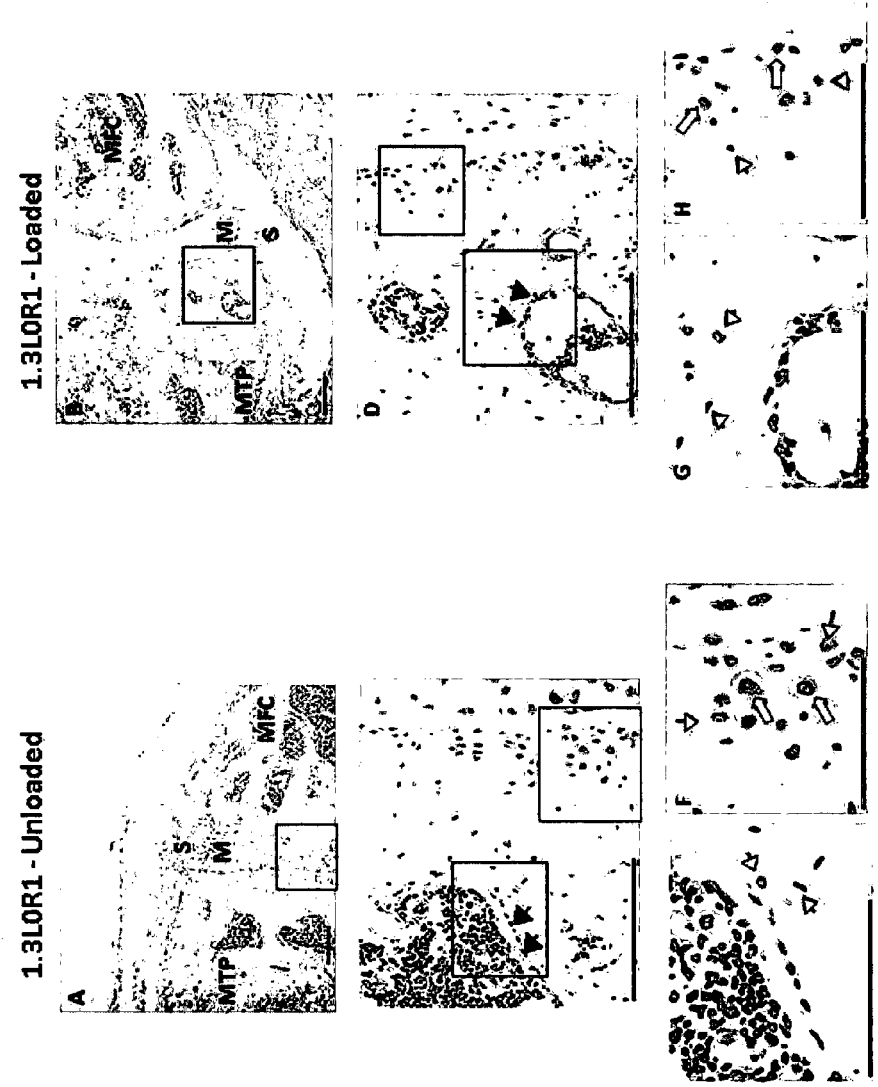
FIG. 15. Kainate 1 immunohistochemistry images taken of the left (unloaded) and right (loaded) knee joints. 1.3L0R1=mouse ID. Images A and B taken at 10× magnification (100 µM scale bars), C and D at 40× magnification (100 µM scale bars) and E, F, G, H taken at 40× magnification (50 µM scale bars), taken on the medial side of the joint, (hollow arrow heads=unstained cells, hollow arrows=stained cells). (MTP=medial tibial plateau, MFC=medial femoral condyle, M=meniscus, S=Synovium). The KA antibody has strong staining in the chondrocytes throughout the cartilage (hollow arrows (F and H)). There is some bone lining cell staining in the unloaded knees (black arrow heads C), with stronger staining in the loaded knees (black arrow heads D). There is almost no staining in the osteocytes. More cells stained positive in the synovium in the loaded knee compared to the unloaded control (A and B).
Figure 16:
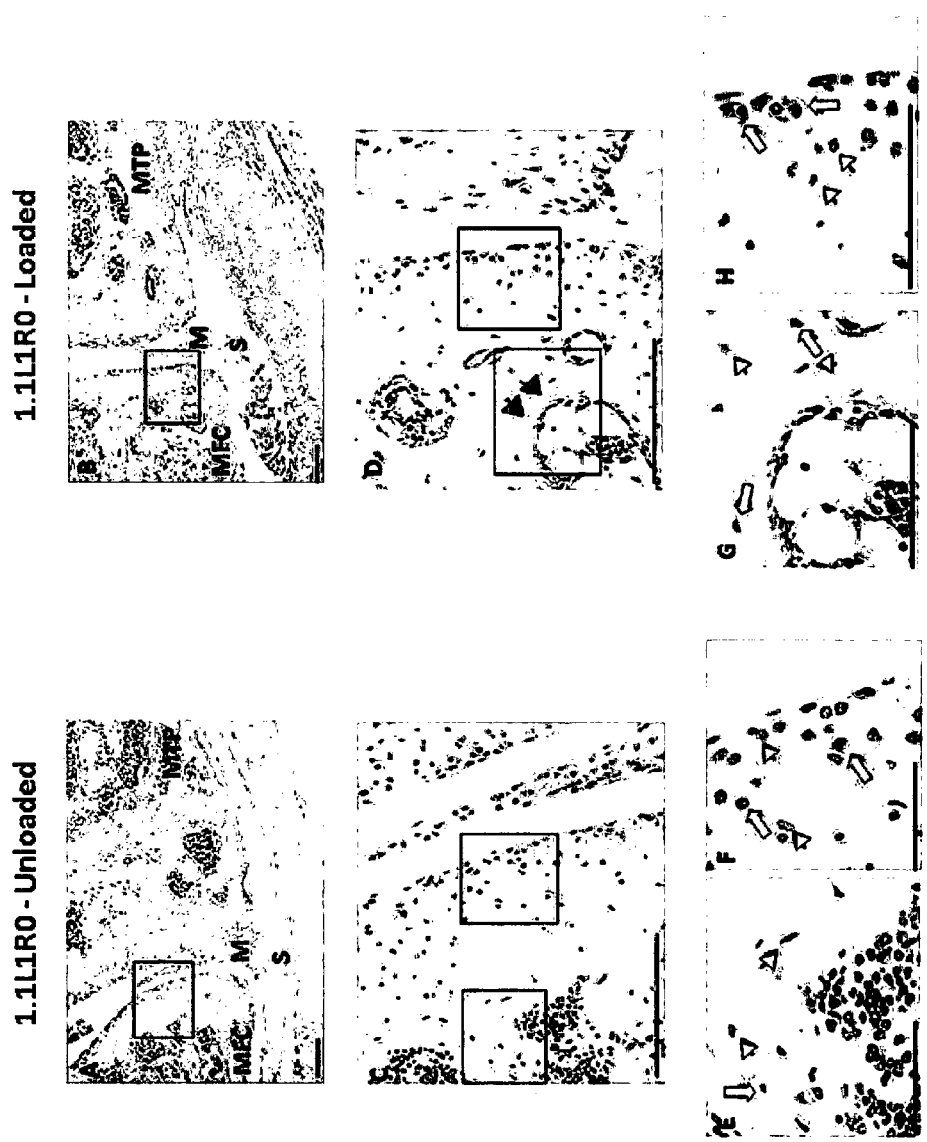
FIG. 16. GluR2 immunohistochemistry images taken of the left (unloaded) and right (loaded) knee joints. 1.1L1R0=mouse ID. Images A and B taken at 10× magnification (100 μM scale bars), C and D and 40× magnification (100 μM scale bars) and E, F, G, H taken at 40× magnification (50 μM scale bars), taken on the medial side of the joint, (hollow arrow heads=unstained cells, hollow arrows=stained cells). (MTP=medial tibial plateau, MFC=medial femoral condyle, M=meniscus, S=Synovium). The GluR2 antibody has strong staining in the chondrocytes throughout the range of the cartilage. Staining was stronger in the bone lining cells in loaded knees (black arrow heads D) compared to unloaded controls (E and G). There is more osteocyte staining, as seen in (E) and (G), but there is little difference between the loaded and non-loaded legs. Synovial staining can also be seen in the loaded (B) compared to unloaded (A)

Immunohistochemistry for EAAC1 (EAAT3) (FIG. 14), KA1 (FIG. 15) and GluR2 (AMPAR2) (FIG. 16) revealed stronger staining on the synovium of loaded knees compared to unloaded controls. Staining was present throughout the joint tissues in both knees but was often stronger in the loaded knee, particularly in the bone.

Discussion

Our data shows that treatment with an AMPA and/or a KA GluR antagonist at the time of joint injury and/or shortly thereafter, to the joint in question, reduces the degenerative pathology, inflammation, and pain associated with the onset or development of post-traumatic OA.

REFERENCES

Introduction
Robert D. Pickering Posttraumatic Arthritis CAN. FAM. PHYSICIAN Vol. 30: July 1984 (1511-1513).
Martel-Pelletier, Lukas M. Wildi & Jean-Pierre Pelletier, (2012) Future therapeutics for osteoarthritis. Bone 51 297-311.
Székely J I, Kedves R, Máté I, Török K, Tarnawa L (1997) Apparent antinociceptive and anti-inflammatory effects of GYKI 52466. Eur J Pharmacol, 1997 Oct. 8; 336(2-3): 143-54.
27. Flood S, Parri R, Williams A, Duance V, Mason D. Modulation of interleukin-6 and matrix metalloproteinase 2 expression in human fibroblast-like synoviocytes by functional ionotropic glutamate receptors. Arthritis and rheumatism 2007; 56(8):2523-34.

Methods
1. Zhang G H, Yoon Y W, Lee K S, Min S S, Hong S K, Park J Y, et al. The glutamatergic N-methyl-D-aspartate and non-N-methyl-D-aspartate receptors in the joint contribute to the induction, but not maintenance, of arthritic pain in rats. Neuroscience letters 2003; 351(3):177-80.
2. Mapp P I, Avery P S, McWilliams D F, Bowyer J, Day C, Moores S, et al. Angiogenesis in two animal models of osteoarthritis. Osteoarthritis and cartilage OARS, Osteoarthritis Research Society 2008; 16(1):61-9.
3. Nowell M A, Williams A S, Carty S A, Schaller J, Hayes A J, Jones G W, et al. Therapeutic targeting of IL-6 trans signaling counteracts STAT3 control of experimental inflammatory arthritis. Journal of immunology 2009; 182 (1):613-22.
4. Klein A, Wessolleck J, Papazoglou A, Metz G A, Nikkhah G. Walking pattern analysis after unilateral 6-OHDA lesion and transplantation of foetal dopaminergic progenitor cells in rats. Behavioural brain research 2009; 199(2): 317-25.
5. Flood S, Parri R, Williams A, Duance V, Mason D. Modulation of interleukin-6 and matrix metalloproteinase 2 expression in human fibroblast-like synoviocytes by functional ionotropic glutamate receptors. Arthritis and rheumatism 2007; 56(8):2523-34.
6. Pfaffl M W. A new mathematical model for relative quantification in real-time RT-PCR. Nucleic acids research 2001; 29(9):e45.
7. Andersen C L, Jensen J L, Orntoft T F. Normalization of real-time quantitative reverse transcription-PCR data: a model-based variance estimation approach to identify genes suited for normalization, applied to bladder and colon cancer data sets. Cancer research 2004; 64(15): 5245-50.
8. Glasson S S, Chambers M G, Van Den Berg W B, Little C B. The OARSI histopathology initiative—recommendations for histological assessments of osteoarthritis in the mouse. Osteoarthritis and cartilage/OARS, Osteoarthritis Research Society 2010; 18 Suppl 3:S17-23.
9. Walsh D A, Bonnet C S, Turner E L, Wilson D, Situ M, McWilliams D F. Angiogenesis in the synovium and at the osteochondral junction in osteoarthritis. Osteoarthritis and cartilage/OARS, Osteoarthritis Research Society 2007; 15(7):743-51.

Tables
Jean Y H et al. Increase in excitatory amino acid concentration and transporters expression in osteoarthritic knees of anterior cruciate ligament transected rabbits. Osteoarthritis Cartilage. 2008; 16, 1442-9.
McNearney T et al. Excitatory amino acid profiles of synovial fluid from patients with arthritis. J Rheumatol. 2000; 27, 739-45.
Jean Y H et al. Increased concentrations of neuro-excitatory amino acids in rat anterior cruciate ligament-transected knee joint dialysates: a microdialysis study. J Orthop Res. 2005; 23, 569-75.
Lawand N B et al. Amino acid release into the knee joint: key role in nociception and inflammation. Pain, 2000; 86, 69-74.
Hajati A K et al. Temporomandibular joint bone tissue resorption in patients with early rheumatoid arthritis can be predicted by joint crepitus and plasma glutamate level. Mediators Inflamm, 2010.

Trang L E et al. Plasma amino acids in rheumatoid arthritis. Scand J Rheumatol. 1985; 14, 393-42.

TABLE 1

Joint degradation scoring system.

| 1.1. Component | 1.2. Sub-component | 1.2.1. Grade |
|---|---|---|
| Cartilage surface integrity | Normal | 0 |
| | Surface irregularities | 1 |
| | Pannus and surface irregularities | 2 |
| | Clefts to middle zone | 3 |
| | Clefts to deep zone | 4 |
| | Clefts to calcified zone | 5 |
| | Complete disorganisation | 6 |
| Chondrocyte appearance | Normal | 0 |
| | Irregular cell organisation | 1 |
| | Cellular organisation highly varied. e.g. highly cellular/acellular | 2 |
| Proteoglycan loss | Normal | 0 |
| | Slight reduction | 1 |
| | Moderate reduction | 2 |
| | Severe reduction | 3 |
| | No dye noted | 4 |
| Tidemark integrity | Intact | 0 |
| | Tip of bone or vessel touching | 1 |
| | Significant contact/breach | 2 |
| Bone changes | None | 0 |
| | Mild | 1 |
| | Moderate | 2 |
| | Severe | 3 |
| TOTAL | | 0-17 |

TABLE 2

GluR, EAAT and IL6 primers and cycling conditions for QRT-PCR.

| Gene (Glu Receptor) | Primers (5'-3') | Annealing temp. (°C.) | Amplicon size | Primer conc. (μm) | $MgCl_2$ conc. (mM) |
|---|---|---|---|---|---|
| Gria1 (AMPAR1) | F-CGAGTTCTGCTACAAATCCCG (SEQ ID NO: 1) R-TGTCCGTATGGCTTCATTGATG (SEQ ID NO: 2) | 61 | 91 bp | 0.2 | 2.5 |
| Gria2 (AMPAR2) | F-GGAAGTAAGGAAAAGACCAGTGCCCTC (SEQ ID NO: 3) R-TTGCCAAACCAAGGCCCCCG (SEQ ID NO: 4) | 60 | 85 bp | 0.2 | 3.5 |
| Gria3 (AMPAR3) | F-GGCAGGAAAAGCGATACTTG (SEQ ID NO: 5) R-CCAGGTTAGCGAGCATGTAG (SEQ ID NO: 6) | 60 | 116 bp | 0.2 | 2.5 |
| Grik1 (GluR5) | F-TGAGCAGTGTCTCTCTTTCAATGCC (SEQ ID NO: 7) R-TCTCTGAGTTCGTCTCTGGTGACAA (SEQ ID NO: 8) | 62 | 145 bp | 0.1 | 2.5 |
| Grik2 (GluR6) | F-AAACCCTGGCGCTTCGGGAC (SEQ ID NO: 9) R-GCCACTGGCTGGATCCCACG (SEQ ID NO: 10) | 62 | 180 bp | 0.1 | 3.5 |
| Grik3 (GluR7) | F-CGCTTCGGTGGCCGCTTCAT (SEQ ID NO: 11) R-CCCCGACCTTCTCGAGGCCA (SEQ ID NO: 12) | 64 | 151 bp | 0.1 | 2.5 |
| Grik4 (KA1) | F-GAACTTGGGATGGTGTCAGC (SEQ ID NO: 13) R-AGAAAGCATGGGATTGGTTG (SEQ ID NO: 14) | 64 | 135 bp | 0.1 | 3.5 |
| Grik5 (KA2) | F-GCCCTCCGTCCCACCAGGAT (SEQ ID NO: 15) R-GACAGCACCTGGCAGCTGGG (SEQ ID NO: 16) | 62 | 137 bp | 0.1 | 2.5 |
| Grin1 (NMDAR1) | F-CCGGGTCATCATCCTTTCT (SEQ ID NO: 17) R-TTCTTGCCATTGATGAGCTG (SEQ ID NO: 18) | 59 | 180 bp | 0.2 | 3.5 |
| Il6 | F-CCGGAGAGGAGACTTCACAG (SEQ ID NO: 19) R-ACAGTGCATCATCGCTGTTC (SEQ ID NO: 20) | 61 | 161 bp | 0.1 | 3.5 |

TABLE 2-continued

GluR, EAAT and IL6 primers and cycling conditions for QRT-PCR.

| Gene (Glu Receptor) | Primers (5'-3') | Annealing temp. (° C.) | Amplicon size | Primer conc. (μm) | MgCl$_2$ conc. (mM) |
| --- | --- | --- | --- | --- | --- |
| EAAT1 (+ 1ex9skip) | F-ACCGCTGTCATTGTGGGTA (SEQ ID NO: 21) R-GTTCCCCAGGAAAGGAGAAG (SEQ ID NO: 22) | 60 | 94 bp | | |
| EAAT1 (+ 1a) | F-CATTAACATGGATGGGACTGC (SEQ ID NO: 23) R-CAGCTGTGGCTGTGATGC (SEQ ID NO: 24) | 60 | 119 | | |
| EAAT1 (span exon9) | F-CTGCCCTCTATGAGGCTTTG (SEQ ID NO: 25) R-TCTCCCAGTACGTTGGTGGT (SEQ ID NO: 26) | 60 | 256 (EAAT1) 121 (ex9skip) | | |
| EAAT1 (span exon3) | F-TTTGGCCAAGAAGAAAGTGC (SEQ ID NO: 27) R-CCATCTTCCCTGATGCCTTA (SEQ ID NO: 28) | 60 | 278 (EAAT1) 140 (EAAT1a) | | |
| EAAT1a | F-CGCTGTCATTGTGGGAAT (SEQ ID NO: 29) R-CACAGCAATGATGGTGGTAG (SEQ ID NO: 30) | 60 | 100 | | |
| EAAT1ex9 skip | F-CGGACAAATTATTACAATCAGGGA (SEQ ID NO: 31) R-CGTGACAAGTGCTCCACAAT (SEQ ID NO: 32) | 60 | 93 | | |
| KA1 | F-GACTGCAGAAACCATGTGTCAGATCC (SEQ ID NO: 33) R-GGTGCAGTTGAAGAAGTTCAGGATCC (SEQ ID NO: 34) | 56 | 247 | | |

TABLE 3

Comparative joint Glutamate concentration in different species with or without disease.

| Animal | Location | Glutamate conc. |
| --- | --- | --- |
| Rabbit | Knee (synovial fluid) | 10, 20 and 30 weeks following ACL transection. Baseline = 4.23 μM, week 10 = 6.27 μM, week 20 = 7.91 μM, week 30 = 9.71 μM. Jean et al (2008) |
| Human | Knee (synovial fluid) | Post-mortem = 6.25 μM, RA = 326 μM, OA = 266 μM. McNearney et al (2000) |
| Rat | Knee (synovial fluid) | 20 weeks following ACL transection. 92% increase compared to the contralateral sham-operated knee. Jean et al (2005). |
| Rat | Knee (synovial fluid) | During initial 10 minutes after kaolin/carrageenan arthritis induction, glutamate concentration increased significantly from 2.72 μM to 5.91 μM. Lawand et al (2000). |
| Human | Blood plasma | Blood samples from patients with early RA. Mean plasma glutamate concentration was 4.1 μmol/L. Hajati et al (2010). |
| Human | Blood plasma | Sex and age matched healthy controls compared to RA patients, Glutamate concentration in controls = 40.15 μmol/L, glutamate concentration in RA = 67.70 μmol/L P < 0.001 Trang L E et al. (1985). |

The invention claimed is:

1. A method of treating post-traumatic osteoarthritis (OA), comprising administering an AMPA and/or a KA GluR antagonist to a damaged joint of an individual at or about the time said joint is damaged.

2. The method as claimed in claim 1 wherein said disease is post-traumatic osteoarthritis in either an early stage (degenerative joint disease) or a late stage (advanced OA).

3. The method as claimed in claim 1, including providing said AMPA and/or KA GluR antagonist as a combination therapeutic comprising at least one further therapeutic useful in treating post-traumatic OA.

4. The method as claimed in claim 1 wherein said antagonist is administered in humans at a dose of about 0.03 mg/kg.

* * * * *